US010632292B2

(12) United States Patent
Forcucci et al.

(10) Patent No.: US 10,632,292 B2
(45) Date of Patent: Apr. 28, 2020

(54) DEVICES AND METHODS FOR TREATING HEART FAILURE

(71) Applicant: CORVIA MEDICAL, INC., Tewksbury, MA (US)

(72) Inventors: Stephen J. Forcucci, Winchester, MA (US); Matthew J. Finch, Medford, MA (US); Christopher J. Magnin, Andover, MA (US); Edward I. McNamara, Chelmsford, MA (US); Carol A. Devellian, Topsfield, MA (US)

(73) Assignee: Corvia Medical, Inc., Tewksbury, MA (US)

( * ) Notice: Subject to any disclaimer, the term of this patent is extended or adjusted under 35 U.S.C. 154(b) by 0 days.

(21) Appl. No.: 14/807,544

(22) Filed: Jul. 23, 2015

(65) Prior Publication Data

US 2016/0022970 A1    Jan. 28, 2016

Related U.S. Application Data

(60) Provisional application No. 62/028,286, filed on Jul. 23, 2014, provisional application No. 62/167,624, filed on May 28, 2015.

(51) Int. Cl.
*A61M 27/00* (2006.01)
*A61B 17/11* (2006.01)
(Continued)

(52) U.S. Cl.
CPC .......... *A61M 27/002* (2013.01); *A61B 17/11* (2013.01); *A61F 2/24* (2013.01); *A61F 2/2478* (2013.01);
(Continued)

(58) Field of Classification Search
CPC ........ A61F 2002/0072; A61F 2002/249; A61F 2/0063; A61F 2/2478; A61F 2/24;
(Continued)

(56) References Cited

U.S. PATENT DOCUMENTS 3,837,345 A    9/1974 Matar
3,874,388 A    4/1975 King et al.
(Continued)

FOREIGN PATENT DOCUMENTS

CN    1218379 A    6/1999
CN    1556719 A    12/2004
(Continued)

OTHER PUBLICATIONS

Celermajer et al.; U.S. Appl. No. 14/498,903 entitled "Apparatus and methods to create and maintain an intra-atrial pressure relief opening," filed Sep. 26, 2014.
(Continued)

*Primary Examiner* — Leslie R Deak
(74) *Attorney, Agent, or Firm* — Shay Glenn LLP

(57) ABSTRACT

A device for implanting into an atrial septum of a patient. In some embodiments, the device has a core region to be disposed in an opening in the atrial septum; a distal retention region adapted to engage tissue on a left atrial side of the septal wall; a proximal retention region adapted to engage tissue on a right atrial side of the septal wall; and a retrieval region comprising a plurality of retrieval members, each retrieval member comprising a connector at a proximal end, the connector being adapted to connect to a delivery system. The device has a delivery configuration and a deployed configuration, the core region, distal retention region and proximal retention region each having a smaller diameter in the delivery configuration than in the deployed configuration, the retrieval member connectors being disposed proxi-
(Continued)

mal to and radially outward from the opening in the deployed configuration.

12 Claims, 13 Drawing Sheets

(51) Int. Cl.
*A61F 2/24* (2006.01)
*A61B 17/00* (2006.01)
*A61B 90/00* (2016.01)
*A61B 17/02* (2006.01)
*A61F 2/00* (2006.01)

(52) U.S. Cl.
CPC . *A61B 17/0218* (2013.01); *A61B 2017/00252* (2013.01); *A61B 2017/00575* (2013.01); *A61B 2017/00592* (2013.01); *A61B 2017/00601* (2013.01); *A61B 2017/00606* (2013.01); *A61B 2017/00623* (2013.01); *A61B 2090/3966* (2016.02); *A61F 2/0063* (2013.01); *A61F 2002/0072* (2013.01); *A61F 2002/249* (2013.01); *A61M 2205/04* (2013.01); *A61M 2210/125* (2013.01)

(58) Field of Classification Search
CPC .......... A61M 2210/125; A61M 27/002; A61M 2205/04; A61B 2017/00575; A61B 2017/00592; A61B 2017/00623
See application file for complete search history.

(56) References Cited

U.S. PATENT DOCUMENTS

| | | |
|---|---|---|
| 4,018,228 A | 4/1977 | Goosen |
| 4,373,216 A | 2/1983 | Klawitter |
| 4,491,986 A | 1/1985 | Gabbay |
| 4,655,217 A | 4/1987 | Reed |
| 4,705,507 A | 11/1987 | Boyles |
| 5,100,423 A | 3/1992 | Fearnot |
| 5,108,420 A | 4/1992 | Marks |
| 5,171,233 A | 12/1992 | Amplatz et al. |
| 5,284,488 A | 2/1994 | Sideris |
| 5,332,402 A | 7/1994 | Teitelbaum |
| 5,334,217 A | 8/1994 | Das |
| 5,387,219 A | 2/1995 | Rapper |
| 5,413,599 A | 5/1995 | Imachi et al. |
| 5,429,144 A | 7/1995 | Wilk |
| 5,433,727 A | 7/1995 | Sideris |
| 5,464,449 A | 11/1995 | Ryan et al. |
| 5,478,353 A | 12/1995 | Yoon |
| 5,488,958 A | 2/1996 | Topel et al. |
| 5,556,386 A | 9/1996 | Todd |
| 5,556,408 A | 9/1996 | Farhat |
| 5,693,090 A | 12/1997 | Unsworth et al. |
| 5,702,412 A | 12/1997 | Popov et al. |
| 5,725,552 A | 3/1998 | Kotula et al. |
| 5,741,297 A | 4/1998 | Simon |
| 5,824,071 A | 10/1998 | Nelson et al. |
| 5,846,261 A | 12/1998 | Kotula et al. |
| 5,876,436 A | 3/1999 | Vanney et al. |
| 5,893,369 A | 4/1999 | Lemole |
| 5,944,738 A | 8/1999 | Amplatz et al. |
| 5,964,754 A | 10/1999 | Osypka |
| 6,050,936 A | 4/2000 | Schweich et al. |
| 6,059,827 A | 5/2000 | Fenton |
| 6,068,635 A | 5/2000 | Gianotti |
| 6,120,534 A | 9/2000 | Ruiz |
| 6,123,682 A | 9/2000 | Knudson et al. |
| 6,123,715 A | 9/2000 | Amplatz |
| 6,152,937 A | 11/2000 | Peterson et al. |
| 6,156,055 A | 12/2000 | Ravenscroft |
| 6,168,622 B1 | 1/2001 | Mazzocchi |
| 6,190,353 B1 | 2/2001 | Makower et al. |
| 6,193,734 B1 | 2/2001 | Bolduc et al. |
| 6,210,338 B1 | 4/2001 | Afremov et al. |
| 6,214,029 B1 | 4/2001 | Thill et al. |
| 6,241,678 B1 | 6/2001 | Afremov et al. |
| 6,258,119 B1 | 7/2001 | Hussein et al. |
| 6,283,983 B1 | 9/2001 | Makower et al. |
| 6,286,512 B1 | 9/2001 | Loeb et al. |
| 6,334,864 B1 | 1/2002 | Amplatz et al. |
| 6,350,277 B1 | 2/2002 | Kocur |
| 6,355,052 B1 | 3/2002 | Neuss et al. |
| 6,355,056 B1 | 3/2002 | Pinheiro |
| 6,357,735 B2 | 3/2002 | Haverinen |
| 6,383,195 B1 | 5/2002 | Richard |
| 6,391,036 B1 | 5/2002 | Berg et al. |
| 6,395,017 B1 | 5/2002 | Dwyer et al. |
| 6,402,777 B1 | 6/2002 | Globerman et al. |
| 6,409,716 B1 | 6/2002 | Sahatjian et al. |
| 6,440,152 B1 | 8/2002 | Gainor et al. |
| 6,454,795 B1 | 9/2002 | Chuter |
| 6,458,153 B1 | 10/2002 | Bailey et al. |
| 6,468,301 B1 | 10/2002 | Amplatz et al. |
| 6,468,303 B1 | 10/2002 | Amplatz et al. |
| 6,527,746 B1 | 3/2003 | Oslund et al. |
| 6,572,652 B2 | 6/2003 | Shaknovich |
| 6,579,311 B1 | 6/2003 | Makower |
| 6,599,308 B2 | 7/2003 | Amplatz |
| 6,626,936 B2 | 9/2003 | Stinson |
| 6,638,257 B2 | 10/2003 | Amplatz |
| 6,645,143 B2 | 11/2003 | Vantassel et al. |
| 6,666,885 B2 | 12/2003 | Moe |
| 6,699,256 B1 | 3/2004 | Logan et al. |
| 6,712,836 B1 | 3/2004 | Berg et al. |
| 6,719,768 B1 | 4/2004 | Cole et al. |
| 6,719,934 B2 | 4/2004 | Stinson |
| 6,837,901 B2 | 1/2005 | Rabkin et al. |
| 6,866,679 B2 | 3/2005 | Kusleika |
| 6,911,037 B2 | 6/2005 | Gainor et al. |
| 6,913,614 B2 | 7/2005 | Marino et al. |
| 6,932,837 B2 | 8/2005 | Amplatz et al. |
| 6,936,058 B2 | 8/2005 | Forde et al. |
| 6,979,343 B2 | 12/2005 | Russo et al. |
| 7,033,372 B1 | 4/2006 | Cahalan |
| 7,037,329 B2 | 5/2006 | Martin |
| 7,044,134 B2 | 5/2006 | Khairkhahan et al. |
| 7,097,653 B2 | 8/2006 | Freudenthal et al. |
| 7,105,024 B2 | 9/2006 | Richelsoph |
| 7,144,410 B2 | 12/2006 | Marino et al. |
| 7,226,466 B2 | 6/2007 | Opolski |
| 7,309,341 B2 | 12/2007 | Ortiz et al. |
| 7,317,951 B2 | 1/2008 | Schneider et al. |
| 7,338,514 B2 | 3/2008 | Wahr et al. |
| 7,350,995 B1 | 4/2008 | Rhodes |
| 7,419,498 B2 | 9/2008 | Opolski et al. |
| 7,445,630 B2 | 11/2008 | Lashinski et al. |
| 7,473,266 B2 | 1/2009 | Glaser |
| 7,485,141 B2 | 2/2009 | Majercak et al. |
| 7,530,995 B2 | 5/2009 | Quijano et al. |
| 7,611,534 B2 | 11/2009 | Kapadia et al. |
| 7,625,392 B2 | 12/2009 | Coleman et al. |
| 7,658,747 B2 | 2/2010 | Forde et al. |
| 7,678,123 B2 | 3/2010 | Chanduszko |
| 7,691,144 B2 | 4/2010 | Chang et al. |
| 7,699,297 B2 | 4/2010 | Cicenas et al. |
| 7,704,268 B2 | 4/2010 | Chanduszko |
| 7,722,629 B2 | 5/2010 | Chambers |
| 7,758,589 B2 | 7/2010 | Ortiz et al. |
| 7,842,026 B2 | 11/2010 | Cahill et al. |
| 7,860,579 B2 | 12/2010 | Goetzinger et al. |
| 7,871,419 B2 | 1/2011 | Devellian et al. |
| 7,905,901 B2 | 3/2011 | Corcoran et al. |
| 7,967,769 B2 | 6/2011 | Faul et al. |
| 7,976,564 B2 | 7/2011 | Blaeser et al. |
| 8,010,186 B1 | 8/2011 | Ryu |
| 8,021,359 B2 | 9/2011 | Auth et al. |
| 8,034,061 B2 | 10/2011 | Amplatz et al. |
| 8,043,360 B2 | 10/2011 | McNamara et al. |
| 8,048,147 B2 | 11/2011 | Adams |
| 8,052,750 B2 | 11/2011 | Tuval et al. |
| 8,157,860 B2 | 4/2012 | McNamara et al. |

(56) References Cited

U.S. PATENT DOCUMENTS

| | | |
|---|---|---|
| 8,163,004 B2 | 4/2012 | Amplatz et al. |
| 8,172,896 B2 | 5/2012 | McNamara et al. |
| 8,252,042 B2 | 8/2012 | McNamara et al. |
| 8,303,623 B2 | 11/2012 | Melzer et al. |
| 8,313,505 B2 | 11/2012 | Amplatz et al. |
| 8,361,138 B2 | 1/2013 | Adams |
| 8,366,088 B2 | 2/2013 | Allen |
| 8,398,670 B2 | 3/2013 | Amplatz et al. |
| 8,460,372 B2 | 6/2013 | McNamara et al. |
| 8,696,611 B2 | 4/2014 | Nitzan et al. |
| 8,696,693 B2 | 4/2014 | Najafi et al. |
| 8,740,962 B2 * | 6/2014 | Finch ............ A61B 17/0057 623/1.11 |
| 8,745,845 B2 | 6/2014 | Finch et al. |
| 8,747,453 B2 | 6/2014 | Amplatz et al. |
| 8,752,258 B2 | 6/2014 | Finch et al. |
| 8,777,974 B2 | 7/2014 | Amplatz et al. |
| 8,778,008 B2 | 7/2014 | Amplatz et al. |
| 8,864,822 B2 | 10/2014 | Spence et al. |
| 8,882,697 B2 | 11/2014 | Celermajer et al. |
| 8,951,223 B2 | 2/2015 | McNamara et al. |
| 8,979,923 B2 | 3/2015 | Spence et al. |
| 9,005,155 B2 | 4/2015 | Sugimoto |
| 9,445,797 B2 | 9/2016 | Rothstein et al. |
| 9,681,948 B2 | 6/2017 | Levi et al. |
| 9,724,499 B2 | 8/2017 | Rottenberg et al. |
| 2001/0027287 A1 | 10/2001 | Shmulewitz et al. |
| 2001/0029368 A1 | 10/2001 | Berube |
| 2001/0053932 A1 | 12/2001 | Phelps et al. |
| 2002/0033180 A1 | 3/2002 | Solem |
| 2002/0077698 A1 | 6/2002 | Peredo |
| 2002/0082525 A1 | 6/2002 | Oslund et al. |
| 2002/0082613 A1 | 6/2002 | Hathaway et al. |
| 2002/0095172 A1 | 7/2002 | Mazzocchi et al. |
| 2002/0120277 A1 | 8/2002 | Hauschild et al. |
| 2002/0143289 A1 | 10/2002 | Ellis et al. |
| 2002/0161424 A1 | 10/2002 | Rapacki et al. |
| 2002/0161432 A1 | 10/2002 | Mazzucco et al. |
| 2002/0165606 A1 | 11/2002 | Wolf et al. |
| 2002/0169377 A1 | 11/2002 | Khairkhahan et al. |
| 2002/0173742 A1 | 11/2002 | Keren et al. |
| 2002/0177894 A1 | 11/2002 | Acosta et al. |
| 2002/0183826 A1 | 12/2002 | Dorn et al. |
| 2003/0032967 A1 | 2/2003 | Park et al. |
| 2003/0093072 A1 | 5/2003 | Friedman |
| 2003/0125798 A1 | 7/2003 | Martin |
| 2004/0044351 A1 | 3/2004 | Searle |
| 2004/0078950 A1 | 4/2004 | Schreck |
| 2004/0087937 A1 | 5/2004 | Eggers et al. |
| 2004/0093075 A1 | 5/2004 | Kuehne |
| 2004/0102719 A1 | 5/2004 | Keith et al. |
| 2004/0102797 A1 | 5/2004 | Golden et al. |
| 2004/0111095 A1 | 6/2004 | Gordon et al. |
| 2004/0133236 A1 | 7/2004 | Chanduszko |
| 2004/0143261 A1 | 7/2004 | Hartley et al. |
| 2004/0143262 A1 | 7/2004 | Visram et al. |
| 2004/0143292 A1 | 7/2004 | Marino et al. |
| 2004/0162514 A1 | 8/2004 | Alferness et al. |
| 2004/0176788 A1 | 9/2004 | Opolski |
| 2004/0193261 A1 | 9/2004 | Berreklouw |
| 2004/0206363 A1 | 10/2004 | McCarthy et al. |
| 2004/0220653 A1 | 11/2004 | Borg et al. |
| 2004/0236308 A1 | 11/2004 | Herweck et al. |
| 2004/0243143 A1 | 12/2004 | Corcoran et al. |
| 2004/0267306 A1 | 12/2004 | Blaeser et al. |
| 2005/0015953 A1 | 1/2005 | Keidar |
| 2005/0049692 A1 | 3/2005 | Numamoto et al. |
| 2005/0049697 A1 | 3/2005 | Sievers |
| 2005/0065507 A1 | 3/2005 | Hartley et al. |
| 2005/0065546 A1 | 3/2005 | Corcoran et al. |
| 2005/0065548 A1 | 3/2005 | Marino et al. |
| 2005/0070934 A1 | 3/2005 | Tanaka et al. |
| 2005/0075655 A1 | 4/2005 | Bumbalough et al. |
| 2005/0075665 A1 | 4/2005 | Brenzel et al. |
| 2005/0080400 A1 | 4/2005 | Corcoran et al. |
| 2005/0080430 A1 | 4/2005 | Wright et al. |
| 2005/0096735 A1 | 5/2005 | Hojeibane et al. |
| 2005/0113868 A1 | 5/2005 | Devellian et al. |
| 2005/0131503 A1 | 6/2005 | Solem |
| 2005/0137609 A1 | 6/2005 | Guiraudon |
| 2005/0137686 A1 | 6/2005 | Salahieh et al. |
| 2005/0148925 A1 | 7/2005 | Rottenberg et al. |
| 2005/0159738 A1 | 7/2005 | Visram et al. |
| 2005/0165344 A1 | 7/2005 | Dobak |
| 2005/0187616 A1 | 8/2005 | Realyvasquez |
| 2005/0234537 A1 | 10/2005 | Edin |
| 2005/0240205 A1 | 10/2005 | Berg et al. |
| 2005/0251063 A1 | 11/2005 | Basude |
| 2005/0251187 A1 | 11/2005 | Beane et al. |
| 2005/0267524 A1 | 12/2005 | Chanduszko |
| 2005/0273075 A1 | 12/2005 | Krulevitch et al. |
| 2005/0273124 A1 | 12/2005 | Chanduszko |
| 2005/0288722 A1 | 12/2005 | Eigler et al. |
| 2006/0004323 A1 | 1/2006 | Chang et al. |
| 2006/0009800 A1 | 1/2006 | Christianson et al. |
| 2006/0009832 A1 | 1/2006 | Fisher |
| 2006/0041183 A1 | 2/2006 | Massen et al. |
| 2006/0052821 A1 | 3/2006 | Abbott et al. |
| 2006/0085060 A1 | 4/2006 | Campbell |
| 2006/0095066 A1 | 5/2006 | Chang et al. |
| 2006/0111704 A1 | 5/2006 | Brenneman et al. |
| 2006/0122646 A1 | 6/2006 | Corcoran et al. |
| 2006/0122647 A1 | 6/2006 | Callaghan et al. |
| 2006/0135990 A1 | 6/2006 | Johnson |
| 2006/0136043 A1 | 6/2006 | Cully et al. |
| 2006/0155305 A1 | 7/2006 | Freudenthal et al. |
| 2006/0184088 A1 | 8/2006 | Van Bibber et al. |
| 2006/0210605 A1 | 9/2006 | Chang et al. |
| 2006/0217761 A1 | 9/2006 | Opolski |
| 2006/0224183 A1 | 10/2006 | Freudenthal |
| 2006/0241675 A1 | 10/2006 | Johnson et al. |
| 2006/0241745 A1 | 10/2006 | Solem |
| 2006/0247680 A1 | 11/2006 | Amplatz et al. |
| 2006/0253184 A1 | 11/2006 | Amplatz |
| 2006/0259121 A1 | 11/2006 | Osypka |
| 2006/0276882 A1 | 12/2006 | Case et al. |
| 2007/0005127 A1 | 1/2007 | Boekstegers et al. |
| 2007/0010851 A1 | 1/2007 | Chanduszko et al. |
| 2007/0021739 A1 | 1/2007 | Weber |
| 2007/0027528 A1 | 2/2007 | Agnew |
| 2007/0038295 A1 | 2/2007 | Case et al. |
| 2007/0043431 A1 | 2/2007 | Melsheimer |
| 2007/0088375 A1 | 4/2007 | Beane et al. |
| 2007/0088388 A1 | 4/2007 | Opolski et al. |
| 2007/0118207 A1 | 5/2007 | Amplatz et al. |
| 2007/0123934 A1 | 5/2007 | Whisenant et al. |
| 2007/0129755 A1 | 6/2007 | Abbott et al. |
| 2007/0168018 A1 | 7/2007 | Amplatz et al. |
| 2007/0185513 A1 | 8/2007 | Woolfson et al. |
| 2007/0197952 A1 | 8/2007 | Stiger |
| 2007/0198060 A1 | 8/2007 | Devellian et al. |
| 2007/0209957 A1 | 9/2007 | Glenn et al. |
| 2007/0225759 A1 | 9/2007 | Thommen et al. |
| 2007/0265658 A1 | 11/2007 | Nelson et al. |
| 2007/0270741 A1 | 11/2007 | Hassett et al. |
| 2007/0282157 A1 | 12/2007 | Rottenberg et al. |
| 2008/0015619 A1 | 1/2008 | Figulla et al. |
| 2008/0033425 A1 | 2/2008 | Davis et al. |
| 2008/0033478 A1 | 2/2008 | Meng |
| 2008/0033543 A1 | 2/2008 | Gurskis et al. |
| 2008/0039804 A1 | 2/2008 | Edmiston et al. |
| 2008/0039881 A1 | 2/2008 | Greenberg |
| 2008/0039922 A1 | 2/2008 | Miles et al. |
| 2008/0058940 A1 | 3/2008 | Wu et al. |
| 2008/0071135 A1 | 3/2008 | Shaknovich |
| 2008/0086168 A1 | 4/2008 | Cahill |
| 2008/0103508 A1 | 5/2008 | Karakurum |
| 2008/0109069 A1 | 5/2008 | Coleman et al. |
| 2008/0119891 A1 | 5/2008 | Miles et al. |
| 2008/0125861 A1 | 5/2008 | Webler et al. |
| 2008/0154250 A1 | 6/2008 | Makower et al. |
| 2008/0154302 A1 | 6/2008 | Opolski et al. |
| 2008/0154351 A1 | 6/2008 | Leewood et al. |
| 2008/0154355 A1 | 6/2008 | Benichou et al. |

(56) References Cited

U.S. PATENT DOCUMENTS

| | | |
|---|---|---|
| 2008/0161901 A1 | 7/2008 | Heuser et al. |
| 2008/0172123 A1 | 7/2008 | Yadin |
| 2008/0177381 A1 | 7/2008 | Navia et al. |
| 2008/0183279 A1 | 7/2008 | Bailey et al. |
| 2008/0188880 A1 | 8/2008 | Fischer et al. |
| 2008/0188888 A1 | 8/2008 | Adams et al. |
| 2008/0215008 A1 | 9/2008 | Nance et al. |
| 2008/0221582 A1 | 9/2008 | Gia et al. |
| 2008/0228264 A1 | 9/2008 | Li et al. |
| 2008/0249397 A1 | 10/2008 | Kapadia |
| 2008/0249562 A1 | 10/2008 | Cahill |
| 2008/0249612 A1 | 10/2008 | Osborne et al. |
| 2008/0262592 A1 | 10/2008 | Jordan et al. |
| 2008/0269662 A1 | 10/2008 | Vassiliades et al. |
| 2008/0312679 A1 | 12/2008 | Hardert et al. |
| 2009/0018570 A1 | 1/2009 | Righini et al. |
| 2009/0030495 A1 | 1/2009 | Koch |
| 2009/0054805 A1 | 2/2009 | Boyle |
| 2009/0054982 A1 | 2/2009 | Cimino |
| 2009/0054984 A1 | 2/2009 | Shortkroff et al. |
| 2009/0062841 A1 | 3/2009 | Amplatz et al. |
| 2009/0076541 A1 | 3/2009 | Chin et al. |
| 2009/0082803 A1 | 3/2009 | Adams et al. |
| 2009/0099647 A1 | 4/2009 | Glimsdale et al. |
| 2009/0112050 A1 | 4/2009 | Farnan et al. |
| 2009/0112244 A1 | 4/2009 | Freudenthal |
| 2009/0112251 A1 | 4/2009 | Qian et al. |
| 2009/0171386 A1 | 7/2009 | Amplatz et al. |
| 2009/0177269 A1 | 7/2009 | Kalmann et al. |
| 2009/0187214 A1 | 7/2009 | Amplatz et al. |
| 2009/0209855 A1 | 8/2009 | Drilling et al. |
| 2009/0209999 A1 | 8/2009 | Afremov |
| 2009/0234443 A1 | 9/2009 | Ottma et al. |
| 2009/0264991 A1 | 10/2009 | Paul et al. |
| 2009/0270840 A1 | 10/2009 | Miles et al. |
| 2010/0022940 A1 | 1/2010 | Thompson |
| 2010/0023046 A1 | 1/2010 | Heidner et al. |
| 2010/0023048 A1 | 1/2010 | Mach |
| 2010/0023121 A1 | 1/2010 | Evdokimov et al. |
| 2010/0030259 A1 | 2/2010 | Pavcnik et al. |
| 2010/0030321 A1 | 2/2010 | Mach |
| 2010/0049307 A1 | 2/2010 | Ren |
| 2010/0051886 A1 | 3/2010 | Cooke et al. |
| 2010/0057192 A1 | 3/2010 | Celermajer |
| 2010/0063578 A1 | 3/2010 | Ren et al. |
| 2010/0094335 A1 | 4/2010 | Gerberding et al. |
| 2010/0106235 A1 | 4/2010 | Kariniemi et al. |
| 2010/0114140 A1 | 5/2010 | Chanduszko |
| 2010/0121370 A1 | 5/2010 | Kariniemi |
| 2010/0131053 A1 | 5/2010 | Agnew |
| 2010/0211046 A1 | 8/2010 | Adams et al. |
| 2010/0249490 A1 | 9/2010 | Farnan |
| 2010/0249491 A1 | 9/2010 | Farnan et al. |
| 2010/0268316 A1 | 10/2010 | Brenneman et al. |
| 2010/0274351 A1 | 10/2010 | Rolando et al. |
| 2010/0298755 A1 | 11/2010 | McNamara et al. |
| 2010/0305685 A1 | 12/2010 | Millwee et al. |
| 2010/0324588 A1 | 12/2010 | Miles et al. |
| 2011/0004296 A1 | 1/2011 | Lutter et al. |
| 2011/0022079 A1 | 1/2011 | Miles et al. |
| 2011/0040374 A1 | 2/2011 | Goetz et al. |
| 2011/0071623 A1 | 3/2011 | Finch et al. |
| 2011/0071624 A1 | 3/2011 | Finch et al. |
| 2011/0087261 A1 | 4/2011 | Wittkampf et al. |
| 2011/0093062 A1 | 4/2011 | Cartledge et al. |
| 2011/0106149 A1 | 5/2011 | Ryan et al. |
| 2011/0130784 A1 | 6/2011 | Kusleika |
| 2011/0184439 A1 | 7/2011 | Anderson et al. |
| 2011/0190874 A1 | 8/2011 | Celermajer et al. |
| 2011/0213364 A1 | 9/2011 | Davis et al. |
| 2011/0218479 A1 | 9/2011 | Rottenberg et al. |
| 2011/0257723 A1 | 10/2011 | McNamara |
| 2011/0270239 A1 | 11/2011 | Werneth |
| 2011/0295183 A1 | 12/2011 | Finch et al. |
| 2011/0319806 A1 | 12/2011 | Wardle |
| 2011/0319989 A1 | 12/2011 | Lane et al. |
| 2012/0022427 A1 | 1/2012 | Kapadia |
| 2012/0130301 A1 | 5/2012 | McNamara et al. |
| 2012/0165928 A1 | 6/2012 | Nitzan et al. |
| 2012/0265296 A1 | 10/2012 | McNamara et al. |
| 2012/0289882 A1 | 11/2012 | McNamara et al. |
| 2012/0289971 A1 | 11/2012 | Segermark et al. |
| 2012/0290062 A1 | 11/2012 | McNamara et al. |
| 2012/0290077 A1 | 11/2012 | Aklog et al. |
| 2012/0316597 A1 | 12/2012 | Fitz et al. |
| 2013/0030521 A1 | 1/2013 | Nitzan et al. |
| 2013/0041359 A1 | 2/2013 | Asselin et al. |
| 2013/0165967 A1 | 6/2013 | Amin et al. |
| 2013/0178784 A1 | 7/2013 | McNamara et al. |
| 2013/0184633 A1 | 7/2013 | McNamara et al. |
| 2013/0184634 A1 | 7/2013 | McNamara et al. |
| 2013/0231737 A1 | 9/2013 | McNamara et al. |
| 2013/0253546 A1 | 9/2013 | Sander et al. |
| 2013/0267885 A1 | 10/2013 | Celermajer et al. |
| 2013/0281988 A1 | 10/2013 | Magnin et al. |
| 2014/0012181 A1 | 1/2014 | Sugimoto et al. |
| 2014/0012368 A1 | 1/2014 | Sugimoto et al. |
| 2014/0172074 A1 | 6/2014 | Concagh et al. |
| 2014/0194971 A1 | 7/2014 | McNamara |
| 2014/0257167 A1 | 9/2014 | Celermajer et al. |
| 2014/0277045 A1 | 9/2014 | Fazio et al. |
| 2014/0277054 A1 | 9/2014 | McNamara et al. |
| 2015/0039084 A1 | 2/2015 | Levi et al. |
| 2015/0119796 A1 | 4/2015 | Finch |
| 2015/0148731 A1 | 5/2015 | McNamara et al. |
| 2015/0313599 A1 | 11/2015 | Johnson et al. |
| 2016/0051800 A1 | 2/2016 | Vassiliades et al. |
| 2016/0120550 A1 | 5/2016 | McNamara et al. |
| 2016/0135813 A1 | 5/2016 | Johnson et al. |
| 2017/0273790 A1 | 9/2017 | Vettukattil et al. |
| 2018/0256865 A1 | 9/2018 | Finch et al. |
| 2019/0021861 A1 | 1/2019 | Finch |
| 2019/0269392 A1 | 9/2019 | Celermajer et al. |

FOREIGN PATENT DOCUMENTS

| | | |
|---|---|---|
| CN | 1582136 A | 2/2005 |
| CN | 1780589 A | 5/2006 |
| CN | 101035481 A | 9/2007 |
| CN | 101035488 A | 9/2007 |
| CN | 101292889 A | 10/2008 |
| CN | 101426431 A | 5/2009 |
| CN | 101579267 A | 11/2009 |
| EP | 1264582 A2 | 2/2002 |
| EP | 1480565 A1 | 9/2003 |
| EP | 1470785 A1 | 10/2004 |
| EP | 1849440 A1 | 10/2007 |
| FR | 2827153 A1 | 1/2003 |
| JP | 58-27935 U | 6/1983 |
| JP | H02-277459 A | 11/1990 |
| JP | 2003530143 | 10/2003 |
| WO | WO95/27448 A1 | 10/1995 |
| WO | WO98/08456 A1 | 3/1998 |
| WO | WO98/42403 A1 | 10/1998 |
| WO | WO01/15618 A2 | 3/2001 |
| WO | WO02/094363 A2 | 11/2002 |
| WO | WO2004/019811 A2 | 3/2004 |
| WO | WO2005/048881 A1 | 6/2005 |
| WO | WO2005/048883 A1 | 6/2005 |
| WO | WO2006/127765 A1 | 11/2006 |
| WO | WO2007/054116 A | 5/2007 |
| WO | WO2007/083288 A2 | 7/2007 |
| WO | WO2008/058940 A1 | 5/2008 |
| WO | WO2010/111666 A1 | 9/2010 |
| WO | WO2010/129511 A2 | 11/2010 |

OTHER PUBLICATIONS

Finch; U.S. Appl. No. 14/645,416 entitled "Devices and methods for treating heart failure," filed Mar. 11, 2015.

Ad et al.; A one way valved atrial septal patch: A new surgical technique and its clinical application; The Journal of Thoracic and Cardiovascular Surgery; 111; pp. 841-848; Apr. 1996.

(56) References Cited

OTHER PUBLICATIONS

Althoff et al.; Long-term follow up of a fenestrated amplatzer atrial septal occluder in pulmonary arterial hypertension; Chest; 133(1); pp. 183-185; Jan. 2008.
Atz et al.; Preoperative management of pulmonary venous hypertension in hypoplastic left heart syndrome with restrictive atrial septal defect; the American Journal of Cardiology; 83; pp. 1224-1228; Apr. 15, 1999.
Bailey, Steven R.; Nanotechnology in prosthetic heart valves (presentation); 31 pgs.; 2005 (year of pub. sufficiently earlier than effective US filing date and any foreign priority date).
Bolling, Steven; Direct flow medical—My valve is better (presentation); 21 pgs.; Apr. 23, 2009.
Cheatham, John P.; Intervention in the critically ill neonate and infant with hypoplastic left heart syndrome and intact atrial septum; Journal of Interventional Cardiology; 14(3); pp. 357-366; Jun. 2001.
Coselli, Joseph S.; No! Valve replacement: Patient prosthetic mismatch rarely occurs (presentation); 75 pgs.; Apr. 25, 2009.
Design News; Low power piezo motion; retrieved from the internet (http://www.designnews.com/document.asp?doc_id=229053&dfpPParams=ht_13,aid 229053&dfpLayout=article); 3 pgs.; May 14, 2010.
Gaudiani et al.; A philosophical approach to mirral valve repair (presentation); 28 pgs.; Apr. 24, 2009.
Hijazi, Zayad M.; Valve implantation (presentation); 36 pgs.; May 10, 2007.
Larios et al.; The use of an artificial foraminal valve prosthesis in the closure of interatrial and interventricular septal defects; Chest; 36(6); pp. 631-641; Dec. 1959.
Leon, Martin B.; Transcatheter aortic valve therapy: Summary thoughts (presentation); 19 pgs.; Jun. 24, 2009.
Ling et al.; Implantable magnetic relaxation sensors measure cumulative exposure to cardiac biomarkers; Nat Biotechnol; 29(3); pp. 273-277; Mar. 2011.
McMahon, Jim; Piezo motors and actuators: Streamlining medical device performance; Designfax; Mar. 23, 2010; 5 pgs.; retrieved from the Internet on Jul. 19, 2012 (http://www.designfax.net/enews/20100323/feature-1.asp).
Merchant et al.; Advances in arrhythmia and electrophysiology; implantable sensors for heart failure; Cir Arrhythm Electrophysiol; 3; pp. 657-667; Dec. 2010.
Moses, Jeffrey W.; The good, the bad and the ugly of transcatheter AVR (presentation); 28 pgs.; Jul. 10, 2009.
O'Loughlin et al.; Insertion of a fenestrated amplatzer atrial sestosotomy device for severe pulmonary hypertension; Heart Lung Circ.; 15(4); pp. 275-277; Aug. 2006.
Park et al.; Blade atrial septostomy: Collaborative study; Circulation; 66(2); pp. 258-266; Aug. 1982.
Pedra et al.; Stent implantation to create interatrial communications in patients with complex congenital heart disease; Catheterization and Cardiovascular Interventions; 47; pp. 310-313; Jan. 27, 1999.
Perry et al.; Creation and maintenance of an adequate interatrial communication in left atrioventricular valve atresia or stenosis; The American Journal of Cardiology; 58; pp. 622-626; Sep. 15, 1986.
Philips et al.; Ventriculofemoroatrial shunt: A viable alternative for the treatment of hydrocephalus; J. Neurosurg.; 86; pp. 1063-1066; Jun. 1997.
Physik Instrumente; Piezo for Motion Control in Medical Design and Drug Research (product information); Physik Instrumente (PI) GmbH & Co. KG; 22 pgs.; © Nov. 21, 2010.
Roven et al.; Effect of compromising right ventricular function in left ventricular failure by means of interatrial and other shunts; Am J Cardiol.; 24(2); pp. 209-219; Aug. 1969.
RPI Newswire; Implantable, wireless sensors share secrets of healing tissues; RPI Newswire; 1 pg.; Feb. 21, 2012; retrieved from the internet on Jul. 18, 2012 (http://news.rpi.edu/update.do).
Sambhi et al.; Pathologic Physiology of Lutembacher Syndrome; Am J Cardiol.; 2(6); pp. 681-686; Dec. 1958.
Sommer et al.; Transcatheter creation of atrial septal defect and fontan fenestration with "butterfly" stent technique; Journal of the American college of Cardiology; 33(2); Suppl. A; 3 pgs.; Feb. 1999.
Stone, Gregg W.; Transcatheter devices for mirral valve repair, surveying the landscape (presentation); 48 pgs.; Jul. 10, 2009.
Stormer et al.; Comparative study of in vitro flow characteristics between a human aortic valve and a designed aortic valve and six corresponding types of prosthetic heart valves; Eur Surg Res; 8(2); pp. 117-131; 1976 (year of pub. sufficiently earlier than effective US filing date and any foreign priority date).
Trafton, Anne; Detecting whether a heart attack has occurred; MIT News; 3 pgs.; Feb. 14, 2011; retrieved from the internet Sep. 20, 2014 (http://newsoffice.mit.edu/2011/cardiac-implant-0214).
Watterson et al.; Very small pulmonary arteries: Central end-to-side shunt; Ann. Thorac. Surg.; 52(5); pp. 1132-1137; Nov. 1991.
Webber, Ralph; Piezo Motor Based Medical Devices; Medical Design Technology; 5 pgs.; Apr. 2, 2009; retrieved from the internet on Jul. 19, 2012 (http://mdtmag.com/articles/2009/04/piezo-motor-based-medical-devices).
Forcucci et al.; U.S. Appl. No. 15/346,711 entitled "Retrievable devices for treating heart failure," filed Nov. 8, 2016.
McNamara et al.; U.S. Appl. No. 14/878,710 entitled "Methods, systems, and devices for resizable intra-atrial shunts," filed Oct. 8, 2015.
Sugimoto et al.; U.S. Appl. No. 14/986,409 entitled "Devices and methods for retrievable intra-atrial implants," filed Dec. 31, 2015.

\* cited by examiner

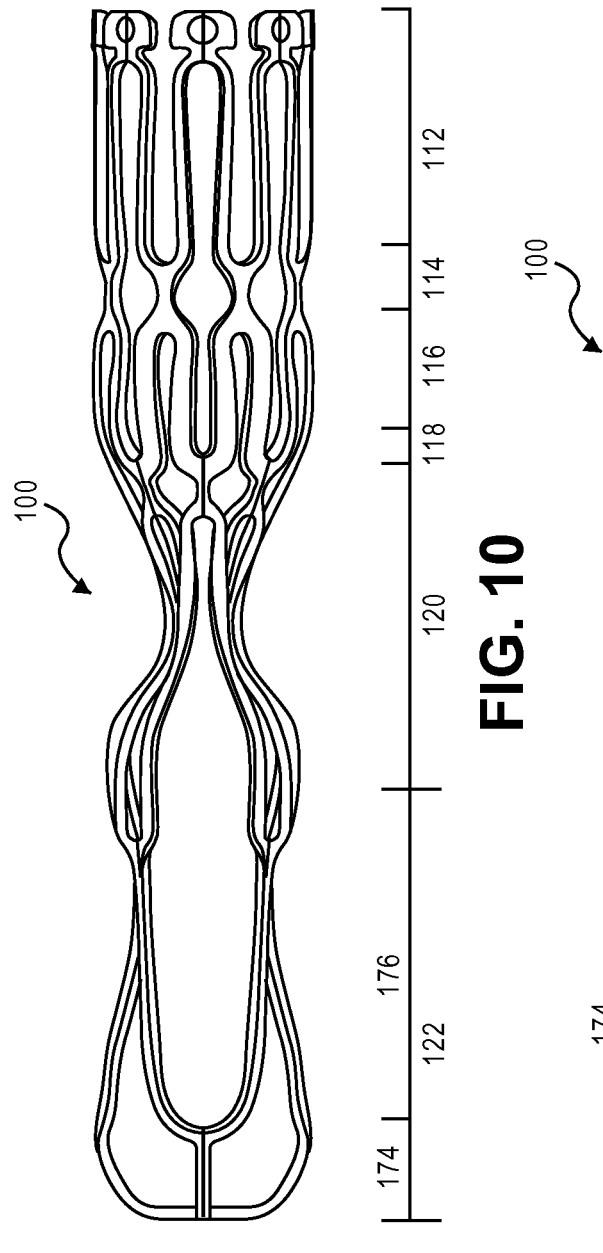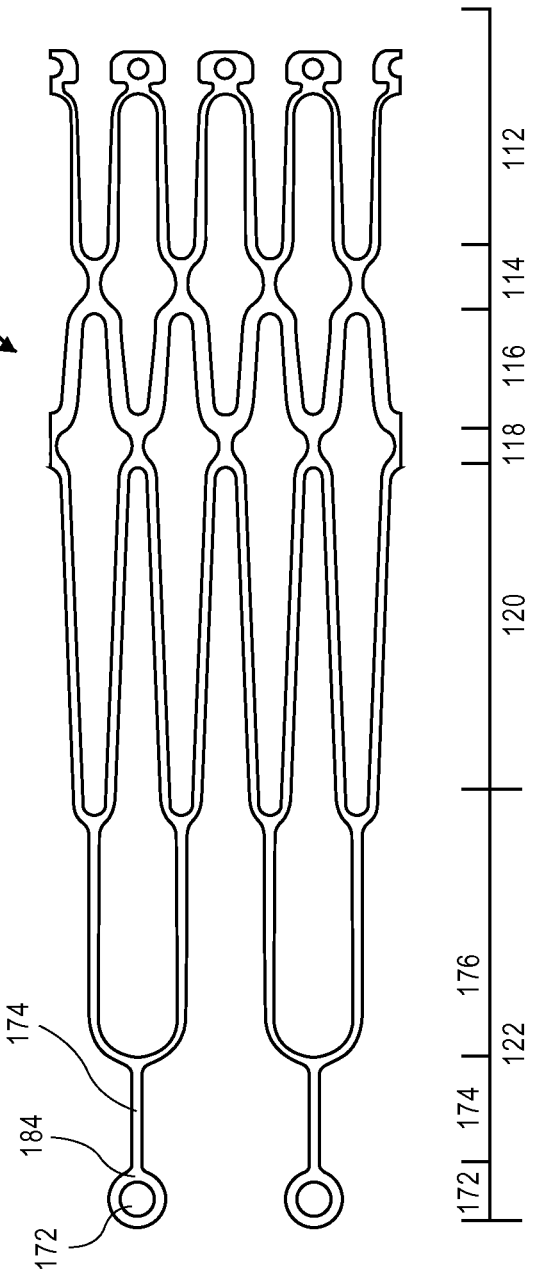
FIG. 10
FIG. 11

DEVICES AND METHODS FOR TREATING HEART FAILURE

CROSS REFERENCE TO RELATED APPLICATIONS

This application claims the benefit under 35 U.S.C. § 119 of U.S. Patent Appl. No. 62/028,286, filed Jul. 23, 2014, and U.S. Patent Appl. No. 62/167,624, filed May 28, 2015, the disclosures of which are incorporated by reference.

INCORPORATION BY REFERENCE

All publications and patent applications mentioned in this specification are incorporated herein by reference in their entirety to the same extent as if each individual publication or patent application was specifically and individually indicated to be incorporated by reference.

FIELD

The present teachings relate to devices and methods of use thereof for treating heart failures. An aspect of the present teachings relates to a device that can be used to change (e.g., reduce) the blood pressure in a heart chamber, for example, by creating a shunt, and optionally regulating the flow of blood through the shunt in order to enhance the therapeutic effect of the shunt. The present teachings further relate to a method of utilizing such a device, for example, in treating congestive heart failure and its related conditions, for example, acute cardiogenic pulmonary edema caused by an elevated pressure in a left side chamber in the heart.

BACKGROUND

Congestive heart failure (CHF) is a condition that affects millions of people worldwide. CHF results from a weakening or stiffening of the heart muscle that commonly is caused by myocardial ischemia (due to, e.g., myocardial infarction) or cardiomyopathy (e.g., myocarditis, amyloidosis). CHF causes a reduced cardiac output and inadequate blood to meet the needs of body tissues.

Treatments for CHF include: (1) pharmacological treatments, (2) assisting systems, and (3) surgical treatments. Pharmacological treatments, e.g., with diuretics, are used to reduce the workload of a heart by reducing blood volume and preload. While pharmacological treatments can improve quality of life, they have little effect on survival. Assisting devices, e.g., mechanical pumps, are used to reduce the load on a heart by performing all or part of the pumping function normally done by the heart. However, in a chronic ischemic heart, high-rate pacing may lead to an increased diastolic pressure, calcium overload, and damages to the muscle fibers. There are at least three surgical procedures for treating a heart failure: (1) heart transplant, (2) dynamic cardiomyoplasty, and (3) the Batista partial left ventriculectomy. These surgical treatments are invasive and have many limitations.

CHF is generally classified into systolic heart failure (SHF) or diastolic heart failure (DHF). In SHF, the pumping action of a heart is reduced or weakened. A normal ejection fraction (EF), the volume of blood ejected out of the left ventricle (stroke volume) divided by the maximum volume remaining in the left ventricle at the end of the diastole or relaxation phase, is greater than 50%. In a systolic heart failure, EF is decreased to less than 50%. A patient with SHF may have an enlarged left ventricle because of cardiac remodeling developed to maintain an adequate stroke-volume. This pathophysiological phenomenon is often associated with an increased atrial pressure and an increased left ventricular filling pressure.

DHF is a heart failure without any major valve disease even though the systolic function of the left ventricle is preserved. Generally, DHF is a failure of the ventricle to adequately relax and expand, resulting in a decrease in the stroke volume of the heart. Presently, there are very few treatment options for patients suffering from DHF. DHF afflicts between 30% and 70% of patients with CHF.

Devices to treat elevated left atrial pressure have been described. For example, U.S. Pat. Nos. 8,740,962 and 8,460,372 both describe prostheses that may be implanted in an opening in the septal wall of the heart to provide a shunt or channel permitting blood to flow from the left atrium into the right atrium. These devices collapse to a smaller configuration for delivery to the heart via a catheter and expand to a larger configuration (e.g., through self-expansion) upon deployment across an opening in the septal wall. Some of these devices have central cores with sufficient radial strength to maintain the patency of the septal wall opening and flexible anchors on both sides of the central core to contact the septal wall for atraumatic anchoring of the device. Some of these devices have retrieval legs and other features providing attachment points for delivery and/or retrieval for possible removal or redeployment.

SUMMARY OF THE DISCLOSURE

During delivery of cardiac pressure-relief devices into openings in the septal wall of the heart, it may be desirable for the clinician to be able to observe the deployed configuration of elements of the device within the heart, such as the anchoring or retention features, prior to releasing the device from the delivery system. In addition, once released from the delivery system, it may be desirable for the portions of the prosthesis that attach to the delivery system to move out of the blood flow path through the prosthesis. If an implanted device must be retrieved after deployment, it may also be desirable for the prosthesis attachment elements to be movable back toward the center of the prosthesis so that the prosthesis can be collapsed and drawn into the retrieval catheter. Also, because the delivery catheter may need to approach the implantation site along an acute angle with respect to the septal wall, it may be desirable for the implant attachment features to be flexible enough to permit the implant to bend away from the longitudinal axis of the catheter during deployment of the implant into the septal wall. Finally, it may be useful for any retrieval features on the device to operate in combination with a strong central core and flexible anchors or retention segments.

One aspect of the invention provides a device for implanting into an atrial septum of a patient, the device having a core region with a plurality of core segments surrounding a central opening, the core region being adapted and configured to be disposed in an opening in the atrial septum; a distal retention region with a plurality of distal retention segments extending from the core segments, the distal retention segments being adapted to engage tissue on a left atrial side of the septal wall; a proximal retention region having a plurality of proximal retention segments extending from the core segments, the proximal retention segments being adapted to engage tissue on a right atrial side of the septal wall; and a retrieval region with a plurality (e.g., two or four) of retrieval members extending from the proximal retention segments, each retrieval member having a connector at a proximal end, the connector being adapted to connect to a delivery system; the device further having a delivery configuration and a deployed configuration, the core region, distal retention region and proximal retention region each having a smaller diameter in the delivery configuration than in the deployed configuration, the retrieval member connectors being disposed proximal to and radially outward from the opening in the deployed configuration.

In some embodiments, the connectors are disposed more radially inward in the delivery configuration than in the deployed configuration. The connectors may be, e.g., eyelets.

In some embodiments, the connectors may extend radially inward from an end of the retrieval members in the deployed configuration. In some embodiments, the connectors may extend distally from an end of the retrieval members in the deployed configuration.

In some embodiments the device also has a retrieval configuration in which the connectors are disposed radially inward from deployed configuration positions and the proximal and distal retention segments are each in substantially same positions as in the deployed configuration. The retrieval members may extend further proximally from the proximal retention region in the delivery configuration than in the retrieval configuration.

Another aspect of the invention provides a method of implanting a pressure relief device in an atrial septum of a patient's heart, in which the device has a distal retention region, a proximal retention region, a core region disposed between the distal retention region and the proximal retention region, an opening through the distal retention region, the core region and the proximal retention region, and a plurality of retrieval members disposed proximal to the proximal retention region. In such embodiments, the method includes the steps of expanding the distal retention region in a left atrium of the patient's heart from a collapsed delivery configuration to a deployed configuration; expanding the core region within an opening in the septal wall between the left atrium and a right atrium of the patient's heart from a collapsed delivery configuration to a deployed configuration; expanding the proximal retention region in the right atrium from a collapsed delivery configuration to a deployed configuration; releasing the retrieval members from a delivery system; and moving the retrieval members to a position radially outward from the opening after the releasing step.

In some embodiments, the moving step includes the step of moving the retrieval members from a position proximal to the opening and radially inward from an outer boundary of the opening to a position radially outward from the outer boundary of the opening. In some embodiments in which the device also has a retrieval configuration in which the retrieval members are in a position in front of the opening and the proximal and distal retention segments are each in substantially same positions as in the deployed configuration, the method includes the further step of expanding the device to the retrieval configuration prior to the releasing step, the steps of expanding the distal retention region, core region and proximal retention region to the deployed configurations being performed after the releasing step.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 10 is a side elevational view of the device of FIG. 7 in a delivery configuration.

FIG. 11 is a flattened view of a portion of the device of FIG. 7.

DETAILED DESCRIPTION

Figure 1:
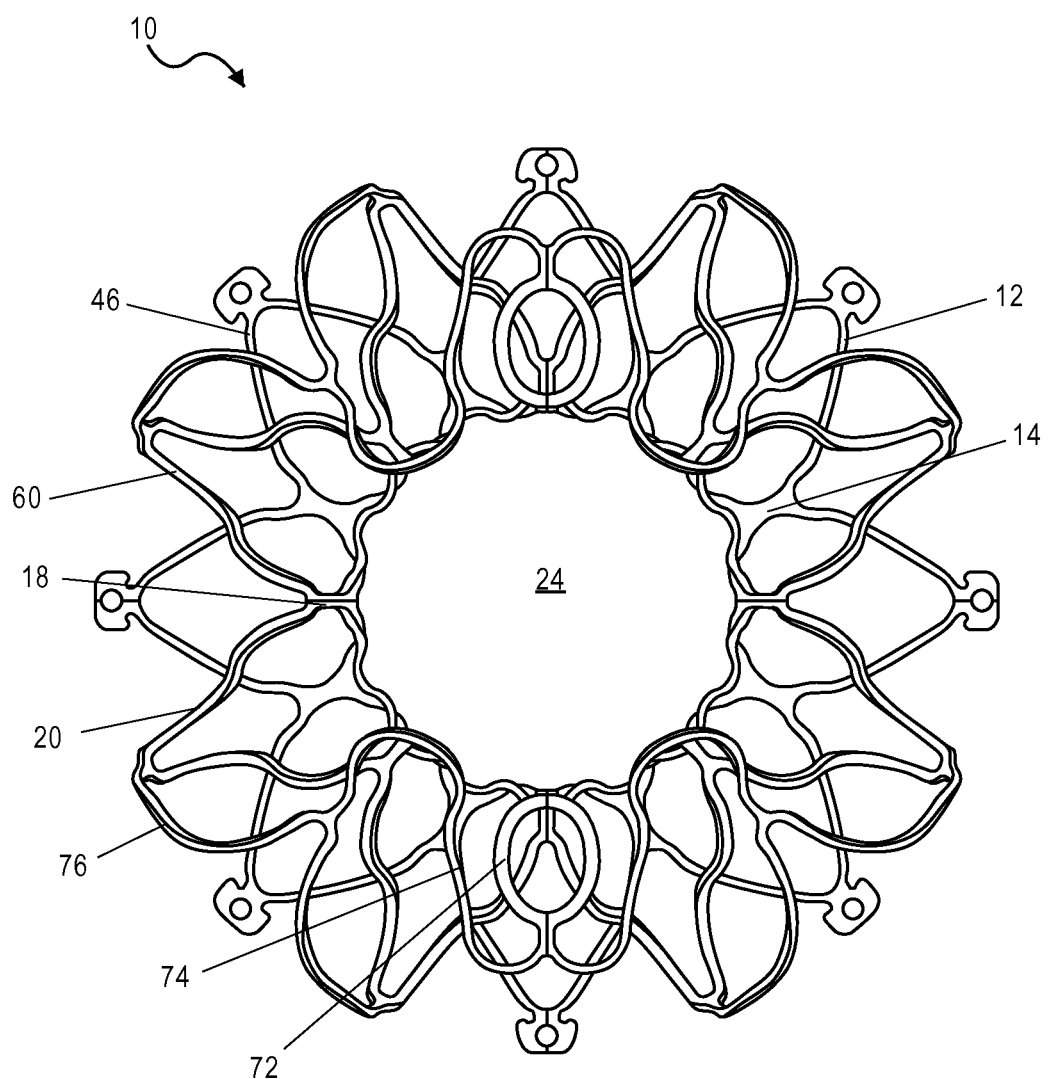
FIG. 1 is a top elevational view of a pressure regulating device according to an embodiment of this invention in a deployed configuration.

The present teachings are described more fully herein with references to the accompanying drawings, which show certain embodiments of the present teachings. The present teachings may, however, be embodied in many different forms and should not be construed as being limited to the embodiments set forth herein. Rather, these embodiments are provided to illustrate various aspects of the present teachings. Like numbers refer to like elements throughout.

The present teachings provide a device and methods of use thereof. For example, the device can be used to regulate the pressure in a heart chamber. Specifically, the device can be used to (a) change an elevated chamber pressure and (b) prevent embolization from the right to left atria in a patient who suffers from CHF or has a Patent Foramen Ovale (PFO) or an Atrial Septal Defect (ASD) but needs a residual flow between the atria so as not to traumatize the heart hemodynamics.

As used herein, when terms "distal" and "proximal" are used to refer portion of the device, they mostly refer to a device in its elongated deliver configuration. The term "proximal" shall mean close to the operator (less into the body) and "distal" shall mean remote from the operator (further into the body). In positioning a medical device from a downstream access point, "distal" is more upstream and "proximal" is more downstream. As used in this application, unless otherwise indicated, the term "aperture" refers to any anatomical anomalies such as PFO, ASD, VSD, or an anatomical feature (such as an opening in the septal wall) created for the purpose of creating a shunt. As used herein, "substantially" means plus or minus 10%.

As explained in further detail below, various embodiments of the present teachings provide methods and devices for regulating the pressure in a heart chamber. In some embodiments, a medical device according to the present teachings includes an open central core region and two retention regions. In some embodiments, the medical device is positioned through an aperture in a septum, creating a shunt, for example, between the left and right atria. In some embodiments, the two retention regions of the medical device are disposed on the opposite sides of the septum. In some embodiments, a medical device according to the present teachings is extended into an elongated profile for a percutaneous delivery and resumes a preset profile in vivo after deployment.

An embodiment of the device in the present teaching has a distal retention portion configured to be positioned against the left atrial side of the septum, a proximal retention portion configured to be positioned against the right atrial side of the septum, and a central core portion disposed between the distal and proximal retention portions and configured to create a conduit for blood to flow through. An embodiment of the device in the present teaching has an elongated configuration for delivering through a catheter system and an expanded configuration securing the device across the septum. In some embodiments, the device is configured to transition from a delivery configuration to a deployed configuration through self-expansion or mechanical actuations. In some embodiments, during deployment, both the distal and proximal retention portions of the device are delivered in radially contracted configurations and expand radially while the device contracts longitudinally. In some embodiments, the central core portion is delivered in a radially contracted configuration and expands radially during deployment. In certain embodiments, one or both of the distal and proximal retention portions of the device contract longitudinally. In various embodiments, one of or both of the deployed distal and proximal retention portions has a generally flange-like profile. In various embodiments, the generally flange-like profile is made of a multiple segments or elements extending in a generally radial configuration from the central core portion. In some embodiments, the deployed distal retention portion is configured to be positioned against one side of the atrial septum. In some embodiments, the deployed proximal retention portion is configured to be positioned against one side of the atrial septum. In certain embodiments, both the deployed distal retention portion and the deployed proximal retention portion are configured to be positioned against both sides of the atrial septum. According to some embodiments, both the deployed distal and proximal retention portions apply a compression force against the septum from both sides, thereby securing the device across the septum.

Figure 2:
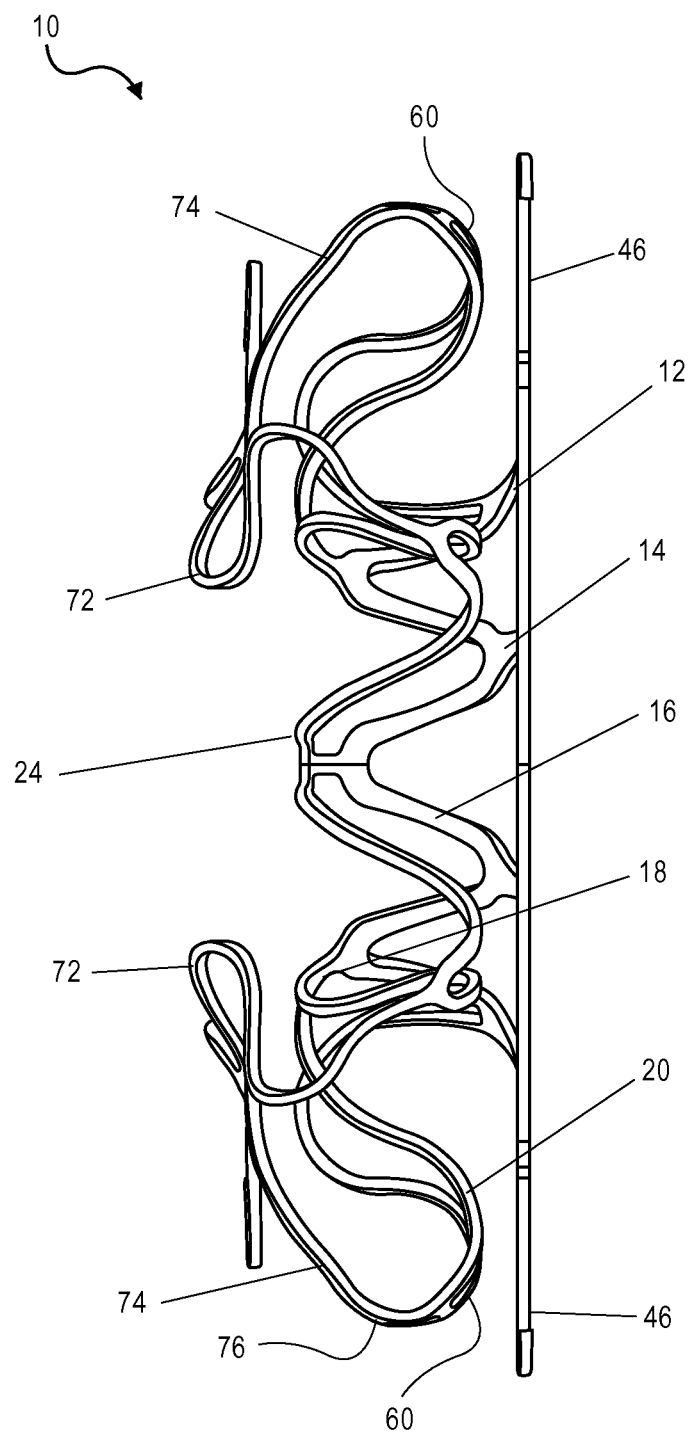
FIG. 2 is a side elevational view of the device of FIG. 1 in the deployed configuration.
Figure 3:
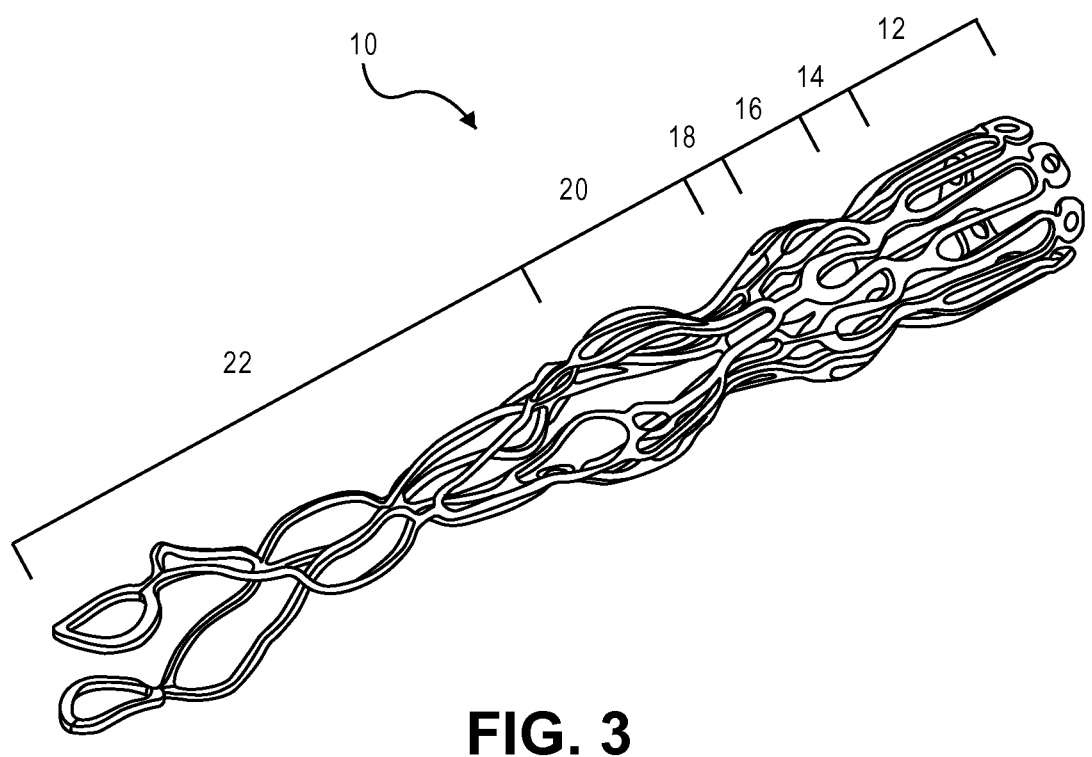
FIG. 3 is a perspective view of the device of FIG. 1 in a delivery configuration.

FIGS. 1-6 show an embodiment of a pressure regulating device 10 according to this invention. FIGS. 1 and 2 show the device 10 in a deployed configuration. FIG. 3 shows device 10 in a delivery configuration. A distal retention region 12 extends distally from a central core region 16 via a distal transition region 14, and a proximal retention region 20 extends proximally from core region 16 via a proximal transition region 18. In the delivery configuration shown in FIG. 3, device 10 (including distal retention region 12, central core region 16 and proximal retention region 20) is radially compressed and axially elongated compared to the deployed configuration shown in FIGS. 1 and 2. Device 10 may be delivered via a delivery catheter (not shown) for deployment in the atrial septum of the patient's heart.

In the deployed configuration shown in FIGS. 1 and 2, the central core region 16 includes an opening 24 to permit blood to flow through the device from the left atrium to the right atrium. When in position in the patient's heart, the radially expanded proximal retention region 20 has a plurality of flexible retention segments 60 that atraumatically engage the septal wall in the right atrium, and the radially expanded distal retention region 12 has a plurality of flexible retention segments 46 that atraumatically engage the septal wall in the left atrium. In some embodiments, the proximal and distal retention regions may cooperate to apply a compressive force to the septal wall. In some embodiments, the proximal and distal retention regions do not apply a compressive force to the septal wall. In some embodiments, the core region may also apply a radially outward force on the portion of the septal wall through which it extends. In other embodiments, the core region does not apply a radially outward force on the portion of the septal wall through which it extends.

In some embodiments, the radial span of the distal retention region 12 in the deployed configuration may be the same as the radial span of the proximal retention region 20. In other embodiments, the radial span of the distal retention region 12 may be greater than the radial span of the proximal retention region to, e.g., account for the typically greater pressure in the left atrium compared to the pressure in the right atrium. In some embodiments, the distal retention region has a general diameter of 8-20 mm upon deployment. In another embodiment, the deployed proximal retention region has a general diameter of 8-20 mm upon deployment. According to some embodiments, upon deployment, the diameter of the deployed core region of the device is about 25-50% of the overall diameter of the deployed distal retention region.

The retrieval region 22 includes retrieval legs 74 extending proximally and radially inwardly from the radially outward ends of the proximal retention segments 60, optionally via intermediate legs 76 disposed between the retrieval leg 74 and the proximal retention segments 60. According to some embodiments, each secondary retrieval leg 76 extends proximally from the proximal end 64 of a proximal retention segment 60. As illustrated, a distal end 78 of a secondary retrieval leg 76 joins the proximal end 64 of a proximal retention segment 60 where two adjacent proximal retention struts 66 join. Loops or eyelets 72 at the proximal ends of the retrieval legs 74 serve as connectors for the delivery and/or retrieval system. As shown in FIGS. 1 and 2, in the device's deployment configuration the eyelets 72 are proximal to and radially outward from the outer boundary of opening 24 and therefore out of the path of any blood flowing through opening 24. In this embodiment, eyelets 72 are oriented in a plane generally perpendicular to the longitudinal axis of the core region 16.

FIG. 3 is a perspective view of device 10 in its collapsed delivery configuration. As shown, the radial dimensions of the proximal retention region 20, central core region 16 and distal retention region 12 are less in the delivery configuration than in the deployed configuration shown in FIGS. 1 and 2. The retrieval leg 74 and eyelets 72 extend proximally from the proximal retention region and connect to a delivery or retrieval system (not shown).

Figure 5:
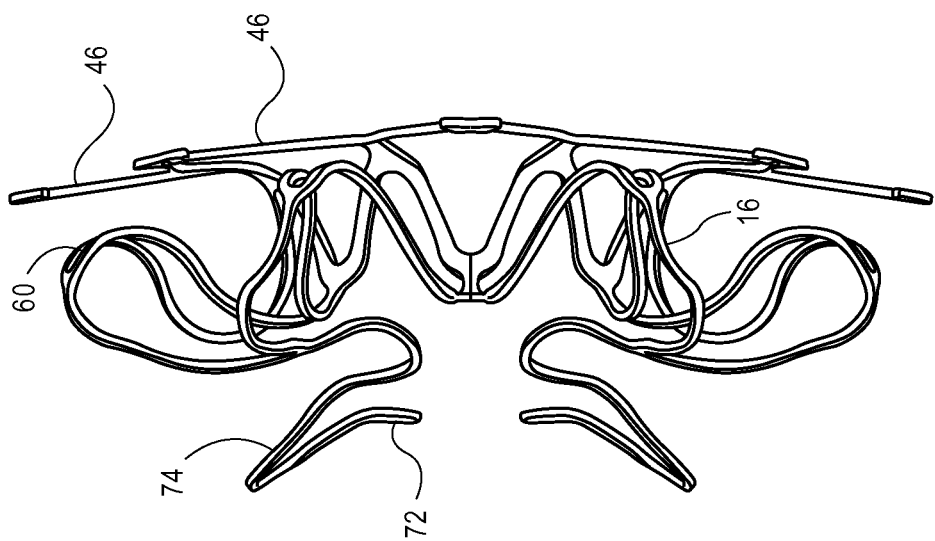
FIG. 5 is a side elevational view of the device of FIG. 1 in the retrieval configuration.
Figure 4:
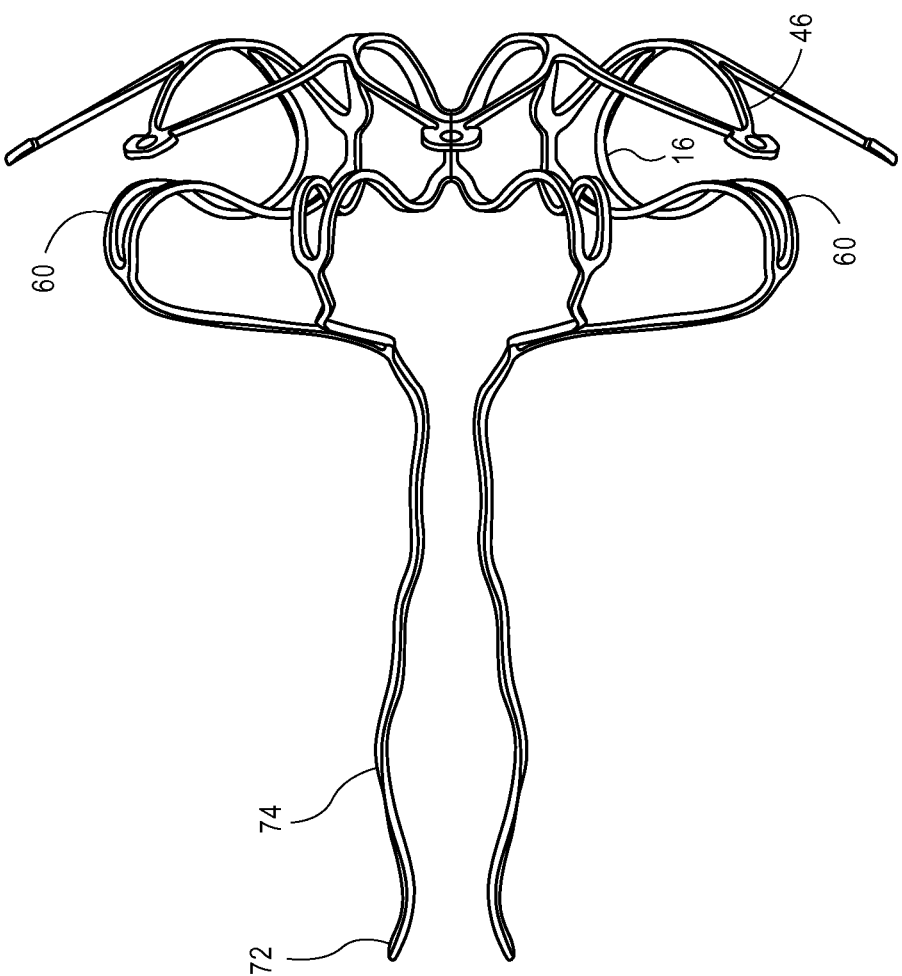
FIG. 4 is a side elevational view of the device of FIG. 1 transitioning from the delivery configuration to a retrieval configuration.

When deploying the device 10 into the septal wall, a delivery system advances device 10 through and out of a catheter. As it emerges from the catheter, the distal retention region 14 of device 10 begins to self-expand in the left atrium. Subsequently, the core region 16 and proximal retention region 20 expand as they emerge from the catheter in the septal wall opening and right atrium, respectively, all while the eyelets 72 of the retrieval legs 74 are still connected to the delivery system. As shown in FIG. 4, distal retention segments 46, core region 16 and proximal retention segments 60 are substantially in their deployed configurations even while retrieval legs 74 extend proximally into the delivery catheter (not shown). In FIG. 5, retrieval legs 74 have emerged from the delivery catheter and have begun moving toward their expanded at-rest shapes; eyelets 72 are radially inward from their at-rest positions because they are still connected to the delivery system. This position is the retrieval configuration of the device 10. After release from the delivery system, retrieval legs 74 and eyelets 72 move radially outward to their at-rest positions radially outside of the devices opening 24 (i.e., the deployed configuration shown in FIG. 1).

When retrieving device 10 for redeployment or removal, the retrieval device grasps eyelets 72, moving them radially inward to the retrieval configuration. Device 10 is then pulled proximally into the retrieval catheter.

Figure 6:
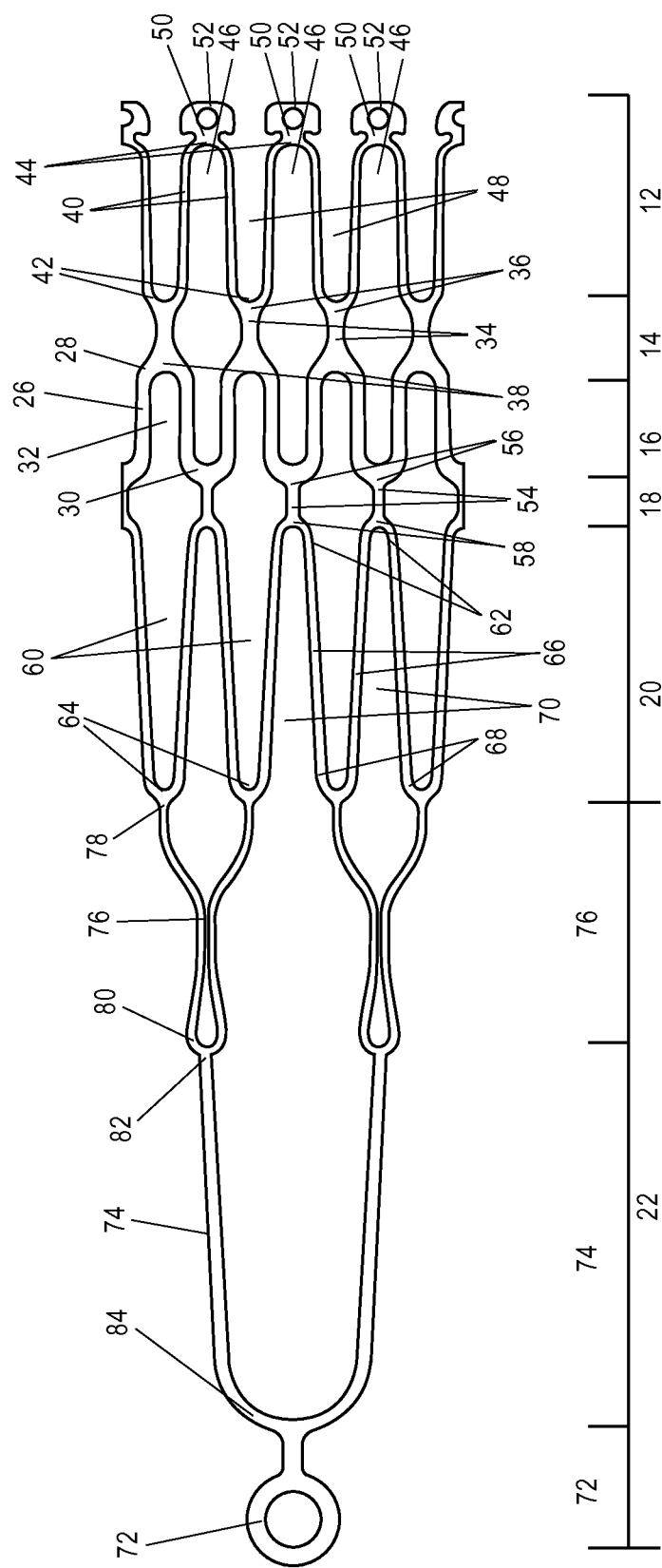
FIG. 6 is a flattened view of a portion of the device of FIG. 1.

FIG. 6 is a two-dimensional view of a portion of the structure of a portion of device 10 in its elongated delivery configuration and in flattened format solely for the purpose of showing various components of the device. As illustrated in FIG. 6, the central core region 16 of the device 10 is formed of a continuous strut 26 in a wavy profile with hairpin turns at each end of the core region 16. As illustrated, the strut 26 extends longitudinally from a first end 28 of the core region 16 toward the second end 30. Upon reaching a second end of the core region 16, the strut makes a "U" turn, then extends longitudinally back to the first send 28. Upon reaching the first end 28 of the core region 16, the strut 26 makes another "U" turn and extends longitudinally and distally toward the second end 30 of the core region 16. This wavy pattern repeats and continues throughout the tubular surface of the core region 16. The ends of the strut 26 join the beginning of the strut 26 to form a closed loop. According to some embodiments, a gap 32 exists between two adjacent portions of the strut 26. According to some embodiments, the profile, including but not limited to shape, width and thickness of the strut 26 may vary at in some locations, either for the purposes of ease of manufacturing or reduced stress concentration after implantation. One skilled in the art should understand that the gap 32 in the delivery configuration is small such that the adjacent portions of the strut 26 are packed tightly close to one another and that the gap 32 in the deployed configuration is enlarged such that the adjacent portions of the strut 26 have moved away from one another so that the core region 16 assumes a larger profile. Core region 16 with a wave strut pattern can be fabricated by cutting a tube by laser or another method known to those skilled in the art.

Additionally, although a wavy pattern with hairpin turn, or "U" turns, has been described in detail in relationship to the core region, other strut designs can also be used without departing from the scope of the present teachings. For example, the wavy pattern could adopt turns closely resembling a "V" shape or other profile. According to alternative embodiments, the core region could adopt either open-cell or closed-cell designs of any patterns known to those skilled in the art. In some embodiments, as the core region transitions from its delivery configuration to its deployed configuration, the diameter of the core region increases and the core region reduces in length, sometimes slightly. In other embodiments, as the diameter of the core region increases, the overall length of the core region remains the same.

In some embodiments of the present teachings, the device 10 in its delivery configuration, such as illustrated in FIG. 3, is configured to be delivered and deployed through a 5 French-12 French catheter. In one embodiment, the elongated device 10 has a diameter ranging from about 1 mm to about 4 mm, and the central core region 16 in a deployed configuration has a diameter ranging from about 3 mm to about 12 mm, or from about 100% to about 300% of that of the core region 16 in its delivery configuration. In other embodiments, the strut 26 of the shunt portion 16 has a width of about 0.005 inch to about 0.030 inch. In a delivery configuration, the gap 32 between two adjacent portions of the strut 26 is from about 0" to about 0.010", and upon deployment, the gap 32 between two adjacent portions of the strut 26 is up to about 0.075".

In some embodiments of the present invention, the device 10 in its delivery configuration, such as illustrated in FIG. 3, has an overall length of about 5-25 mm, with the length of the core region 16 being 0.5-5 mm. In one embodiment, for a deployed device 10, the length of the core region 16 ranges from about 1 mm to about 7 mm, with the overall length of the device 10 ranging from about 3 mm to about 12 mm. In another embodiment, the length of the core region 16 of a deployed device ranges from about 30 to about 70% of the length of the device in the deployed profile.

Referring again to FIG. 6, the distal end 28 of the core region 16 of the device 10 extends from a distal transition portion 14. According to some embodiments, the distal transition portion 14 includes a plurality of distal transition struts 34 each extending from the distal ends 28 of the core region 16 and terminating at the proximal ends 42 of the distal retention segment 46 of the device 10. As illustrated, a proximal end 38 of each distal transition strut 34 joins the core region 16 at the distal end 28 of each hairpin turn, and a distal end 36 of each distal transition struts 34 joins the distal retention segments 46 as shown in FIG. 6. When the device 10 is at its delivery configuration, such as illustrated in FIG. 3, the distal transition portion 14 has a small generally tubular profile with adjacent struts 34 packed closely and parallel to one another. The distal transition portion 14 is also configured to transform from a delivery configuration to a deployed configuration. During such a transition, a distal section of the struts 34 extends radially outwardly, and a proximal section of the struts 34 expands, as the core region 16 expands radially into its deployed profile. Thus, while the device 10 is in its deployed configuration, the distal transition struts 34 bend at a location so that the core region 16 of the device 10 has a tubular profile at or near the proximal end 28 of the distal transition struts 34, and at least a part of the distal retention region 12 of the device 10 has a radially outwardly relatively disc-like profile that is at an angle, sometimes perpendicular, to the longitudinal axis of the core region 16 at the distal end 30 of the distal transition struts 34.

According to some embodiments, as illustrated in FIG. 6, the bending location on the distal transition struts 34 has a narrower width ("waist") than another portion, sometimes the remaining portions, of the struts 34. In some embodiments, the lead-ins from both directions generally have a curved configuration. One skilled in the art should understand that although the bending location has curved lead-ins from both ends, other geometries, shapes, or profiles for narrowing the strut width at the bending location could also be used. Thus, what has been disclosed should not be viewed as limiting to the scope of the present teaching. In one embodiment, the waist has a width from about 0.003" to about 0.015", or from about 30% to about 100% of the width of the widest portion of the distal transition struts 34. Additionally, in order to control the bending direction, the width of the distal transition struts 34 can be greater than the thickness. Additionally, the length of the distal transition portion, as well as the width of the waist could vary according to the overall size of the device and design criteria.

Continuing referring to FIG. 6, the device 10 includes a distal retention region 12. As described herein, the distal retention region 12 of the device 10 has an expanded disc-like profile when the device is deployed, as illustrated in FIG. 1, and a collapsed generally tubular profile during delivery, as illustrated in FIG. 3. Now referring to FIG. 6, the distal retention region 12 includes multiple retention segments 46 each including or formed by two adjacent distal retention struts 40. As shown, two separate struts 40 extend distally from the distal ends 36 of distal transition struts 34. The proximal ends 42 of the two distal retention struts 40 are side by side from each other, with a gap 48 in between. According to one embodiment, the distal ends 44 of two distal retention struts 40 extend from the distal end 36 of two adjacent distal transition struts 34 connected to each other, forming a distal retention segment 46. According to some embodiments, in delivery configuration, the distal retention segment 46 formed by two adjacent distal retention struts 44 is relatively elongated with two adjacent distal retention struts 44 extending close to each other, and in the deployed configuration, the distal retention segment 46 formed by two adjacent distal retention struts 44 is expanded in width with the proximal ends 42 of the two distal retention struts 40 spreading apart and shortened in overall length, with the gap 48 between the two adjacent distal retention struts 44 widening.

According to one embodiment, while the device 10 is in its delivery configuration, the distal retention region 12 radially collapses with each distal retention segment 46 orienting longitudinally along the longitudinal axis of the core region 16. According to one embodiment, while the device 10 is in its deployed configuration, the distal retention segments 46 expand radially with each distal retention segment 46 forming a plane at an angle, for example, perpendicular, to the longitudinal axis of the core region 16. Upon deployment in vivo, the distal retention region 12 is configured to be deployed inside the left atrium with each of the distal retention segments 46 located at the left atrial side of the atrial septum. In certain embodiments, the distal retention opposes the left atrial side of the atrial septum. According to some embodiments, upon deployment, the distal retention region 12 forms a disc-like configuration, with at least a portion, sometimes a substantial portion, of the surface area of each retention segment 46 contacting the atrial septum. In another embodiments, the distal retention region 12 forms an umbrella-like configuration with at least a portion, sometimes a substantial portion, of the surface area of each retention segment 46 doming away from the atrial septum. For example, one or more distal ends of the distal retention segments 46 can contact the atrial septum. In yet another embodiment, the distal retention region 12 forms a generally straight slope profile with at least a portion, sometimes a substantial portion, of the surface area of each distal retention segment 46 not contacting the atrial septum. In this particular embodiment, one or more distal ends of the distal retention segments 46 remain furthest away from the atrial septum. One skilled in the art should understand that other suitable profile could also be used. Thus the exemplary embodiments discussed, shown, or mentioned herein should not be viewed as limiting.

According to some embodiments, the distal ends 50 of each distal retention segment 46 includes a foot 52, as illustrated in FIG. 6. The foot 52 is configured to prevent the distal ends 50 of the distal retention segments 46 from penetrating, piercing, or eroding into the septal tissues. According to some embodiments, the foot 52 is configured to provide a larger surface area for contacting the tissues and/or reducing the force that the distal retention segments 46 apply onto the tissues. In some embodiments, the foot 52 is also configured to incorporate a radiopaque marker. For example, as illustrated in FIG. 6, a radiopaque marker can be wedged into a hole on each of the feet 52.

Continuing referring to FIG. 6, the device 10 includes a proximal transition portion 18. Similar to the distal transition portion 14, the proximal transition portion 18 includes a plurality of proximal transition struts 54 each extending from the proximal end 30 of the core region 16 and terminating at the distal end 62 of the proximal transition strut 66 of the device 10. As illustrated in FIG. 6, a distal end 56 of each proximal transition strut 54 joins the core region 16 at the proximal end 30 of each hairpin turn and joins the proximal retention segments 60 at the distal end 62 of the proximal transition strut 66. When the device 10 is at its delivery configuration, the proximal transition portion 18 has a small generally tubular profile, such as illustrated in FIG. 3, with adjacent struts 54 packing closely and parallel to each other. The proximal transition portion 18 is also configured to transform from a delivery configuration to a deployed configuration. During such transition, a proximal section of the struts 54 extends radially outwardly, and a distal section of the struts 54 expands as the core region 16 expands radially into its deployed configuration. Thus, while the device 10 is in its deployed configuration, the proximal transition struts 54 bend at a location so that the core region 16 of the device has a tubular profile at the distal end 56 of the proximal transition struts 54, and the proximal retention region 20 of the device 10 have a radially outward umbrella-shaped profile that is generally at an angle, sometimes perpendicular, to the longitudinal axis of the core region 16 at the proximal end 58 of the proximal transition struts 54.

According to some embodiments, as illustrated in FIG. 6, the bending location on the proximal transition struts 54 has a narrower width ("waist") than another portion, sometimes the remaining portions, of the struts 54. In some embodiments, the lead-ins from both directions have a generally curved configuration. One skilled in the art should understand that although the bending location has a generally curved lead-ins from both ends of the waist, other geometries, shapes, or profiles for narrowing the strut width at the bending location could also be used. Thus what has been disclosed should not be viewed as limiting. In one embodiment, the waist has a width from about 0.006" to about 0.030", or from about 25 to about 80% of the width of the widest portion of the proximal transition struts 54. In addition, in order to control the bending direction, the width of the proximal transition struts 54 can be greater than the thickness of the proximal transition struts. Additionally, in some embodiments, for example as illustrated in FIG. 6, the proximal transition struts 54 are shorter and narrower than the distal transition struts 34 of the device. One skilled in the art should understand that the proximal transition struts 54 can have the same length and/or width as the distal transition struts 34.

Similar to the distal retention region 12, the device 10 can also have a proximal retention region 20. In some embodiments, the proximal retention region 20 of the device 10 has an expanded umbrella-like profile when deployed, as illustrated in FIG. 1, and a collapsed generally tubular profile during delivery, as illustrated in FIG. 3. Now referring to FIG. 6, the proximal retention region 20 includes multiple proximal retention segments 60. In various embodiments, each of the proximal retention segments is formed by two adjacent proximal retention struts 66. As shown in the figure, two separate struts 66 extend proximally from the proximal end 58 of a proximal transition strut 54. The distal ends 62 of the two proximal retention struts 66 are located side by side from each other with a gap 70 in between. According to one embodiment, the distal ends 62 of two proximal retention struts 66 extended from the proximal end 58 of two adjacent proximal transition struts 54 connects to each other, forming a proximal retention segment 60. According to some embodiments, in a delivery configuration, the proximal retention segment 60 formed by two adjacent proximal retention struts 66 are relatively elongated with two adjacent proximal retention struts 66 extending close to each other; and in deployed configuration, the proximal retention segment 60 formed by two adjacent proximal retention struts 66 are expanded in width and shortened in the overall length with the gap 70 between two adjacent proximal retention struts 66 widened.

According to one embodiment, when the device 10 is in its delivery configuration, the proximal retention portion 20 radially collapses with the proximal retention segments 60 orienting longitudinally along the longitudinal axis of the core region 16, and when the device 10 is in its deployed configuration, the proximal retention portion 20 radially expands with the proximal retention segment 60 curving distally, for example as illustrated in FIG. 1. When the device is deployed in vivo, according to some embodiments, for example as illustrated in FIG. 2, a first section of each proximal retention segment 60 curves distally toward the atrial septum forming a first curve, a second section of each proximal retention segment 60 curves proximally away from the atrial septum forming a second curve, with a portion of each proximal retention segment 60 between the first and second sections of each proximal retention segment 60 contacting the septal tissue.

The curved deployment configuration of the proximal retention region 20 allows the device to accommodate various atrial septum thickness. For example, for a thin atrial septum, the curved proximal retention segments 60 can fully assume its pre-defined curved deployment configuration. For a thick atrial septum, the curved proximal retention segments 60 can oppose the atrial septum, and when the septum pushes back, the curved proximal retention segments 60 can deflect at their first curve while maintaining the device 10 in place.

According to some embodiments, curving the second section of the deployed proximal retention region 20 away from the atrial septum enlarges the contacting surface area with the septal tissue, thereby preventing any trauma to the tissue. One skilled in the art should understand, the second curve of the proximal retention segments 60 can start at any location near or at the proximal ends 64 of each retention segment 60.

According to some embodiments, in a delivery configuration, the proximal retention region struts 66 have a similar width as the distal retention struts 40. In other embodiments, the proximal retention struts 66 have a different width than the distal retention struts 40. In yet another embodiment, the width of the strut 26 of the core region 16 is greater than that of the proximal retention struts 66 and that of the distal retention struts 40, so that the core region 16 is more rigid than the proximal and distal retention portions 12, 20. According to one embodiment of the present teachings, upon deployment, the stiff core region 16 pushes the surrounding tissue radially outwardly, thereby maintaining the size of the opening for the treatment, while the relative pliable proximal and distal retention portions 12, 20 gently contact the septal tissue without penetration.

According to some embodiments, at least some of the proximal retention struts 66 are longer than some of the distal retention struts 40. In some embodiments, all of the proximal retention struts are longer than the distal retention struts. In some embodiments, the distal retention struts 40 have a length of about 2-7 mm. In some embodiments, the proximal retention struts 66 have a length of about 2-14 mm. One skilled in the art should understand that the specific length of the distal retention struts 40 and/or proximal retention struts 66 should be determined by, inter alia, the overall size of the device, which in turn is determined by the needs of a patient. According to some embodiments, the proximal retention struts 66 are configured so that, upon full deployment, its first section curves toward the septum, forming a space between a portion of the strut and septum, and the most radially outward portion of the proximal retention struts 66 is at or near the most radially outward portion of the distal retention struts 40 on the opposite side of the septum.

In various embodiments, the device 10 is fabricated from a tube. Thus, all portions of the device 10, such as the distal retention portion 12, the distal transitional portion 14, the core region 16, the proximal transitional portion 18, the proximal retention portion 20, and proximal retrieval portion 22, have a same thickness. In one embodiment, the thickness of the tube, and thus the thickness of each portion of the device, is from 0.005-0.007 inch. In another embodiment, at least one portion of the device 10 has a different thickness than the rest of the device. This, in some circumstances, can be achieved by removing material from other portions.

According to one embodiment, as illustrated in FIG. 3, while the device 10 is in its delivery configuration, the secondary retrieval legs 76 orient longitudinally along the longitudinal axis of the core region 16. In some embodiments, two adjacent secondary retrieval legs 76 extend close to each other. When the device 10 is in its deployed configuration, as illustrated in FIG. 1, the secondary retrieval strut 76 extends radially inwardly, forming a curved profile with the distal ends of the secondary retrieval legs 76 located at a radially outward location, and the proximal of the secondary retrieval legs 76 located at a radially inward location relative to the distal end of the secondary retrieval legs 76. According to some embodiments, in a deployed profile, the distal ends of the secondary retrieval legs 76 are separate from one another, as each of the distal ends connecting to the proximal end of a deployed proximal retention segment 60. The proximal ends of the secondary retrieval legs 76 are configured to be at locations radially inward from the distal ends of the secondary retrieval legs 76 and radially outward from the opening 24 of the deployed core region 16. One skilled in the art should know, although exemplary embodiments described herein and illustrated in figures disclose secondary retrieval legs 76 in a curved profile, specific designs of the deployed secondary retrieval legs 76 can be in any profiles that are suitable for the corresponding applications. Thus, the embodiments herein should not be viewed as limiting to the scope of the present teachings. According to some embodiments, as shown in FIG. 2, the deployed secondary retrieval legs 76 are proximal to the deployed proximal retention segments 60. Looking from the proximal end of a deployed device, as illustrated in FIG. 1, every two joined deployed secondary retrieval legs 76 are located between two deployed proximal retention segments 60.

In one embodiment, the width of each portion, such as the distal retention portion 12, the distal transitional portion 14, the core region 16, the proximal transitional portion 18, the proximal retention portion 20, and proximal retrieval portion 22, of the device 10 is the same as the thickness of the portion. In another embodiment, the width of the distal retention portion 12, the distal transitional portion 14, the core region 16, the proximal transitional portion 18, and the proximal retention portion 20, are greater than the thickness of these portions. In some embodiments, the width of the proximal retrieval portion 22 is the same as the thickness. According to some embodiments, for portions of the device having a width greater than the thickness, the curving and bending of such portions can be achieved in a controlled manner, without risking the struts being twisted during the process. For other portions of the device where twisting is expected, or less concerning, such as the proximal retrieval portion, the thickness and width can be the same. According to some embodiments, the thickness of each portion of the device ranges from about 0.003" to about 0.09".

According to some embodiments, the retrieval eyelets 72 are configured to be attached to a flexible delivery mechanism. In one embodiment (not shown), a delivery filament, such as a wire or a suture, extends through one or more retrieval attachment mechanisms with both ends of the filament being controlled by a clinician. Upon deployment, one end of the delivery filament is loosened and the other end of the delivery filament is retracted proximally so that the entire flexible delivery filament is removed from the body. One skilled in the art would understand that a flexible delivery filament allows the device fully deploy at a treatment location, while still under the control of the clinician, so that the deployment can be assessed and the device can be retrieved if necessary.

According to some embodiments, the retrieval eyelets 72 are configured to be attached to a relatively rigid delivery mechanism. In one embodiment (not shown), a delivery shaft with notches at its distal end for hosting the retrieval eyelets 72. During delivery, the retrieval eyelets 72 is secured inside the notch, and upon deployment, the retrieval eyelets 72 are released from the notch. One skilled in the art would understand that a relatively rigid delivery shaft can push the device distally inside the delivery catheter and to deploy device.

According to some embodiments, the device 10 includes eight proximal retention segments 60, eight secondary retrieval legs 76, four primary retrieval legs 74, and two retrieval attachment mechanisms 72. Each retrieval attachment mechanism 72 joins a proximal junction formed by two adjacent primary retrieval legs 74. Each distal end 82 of the two adjacent primary retrieval legs 74 further joins a proximal junction 80 formed by two adjacent secondary retrieval legs 76. Each distal end 78 of the said two adjacent secondary retrieval legs 76 joins a proximal end 64 of a proximal retention segment 60. Although FIG. 6 illustrates the proximal ends 84 of two adjacent primary retrieval legs 74 joining each other first and then joining the retrieval attachment mechanism 72, one skilled in the art should understand that the proximal ends 84 of two adjacent primary retrieval legs 74 could join a retrieval attachment mechanism 72 individually, without joining to each other first. Thus, the exemplary illustration should not be viewed as limiting.

According to one embodiment of the present teachings, the device 10 is pre-set into its deployed profile and stretched into an elongated profile, such as shown in FIG. 3, for percutaneous delivery. Upon deployment, the device will recover to its pre-set deployed configuration once free from constraint of the delivery catheter. To minimize any deformation during the delivery process, according to one embodiment of the present teachings, the maximum ratio of the thickness (t) of a curved portion of the device (e.g., the transition from proximal retention segments 60 to secondary retrieval legs 76) over two times of the radius "R" of that curved portion is 0.12, i.e., $t/2R \leq 12\%$. Maintaining this ratio will ensure the maximum recovery of the intended curvature.

Figure 7:
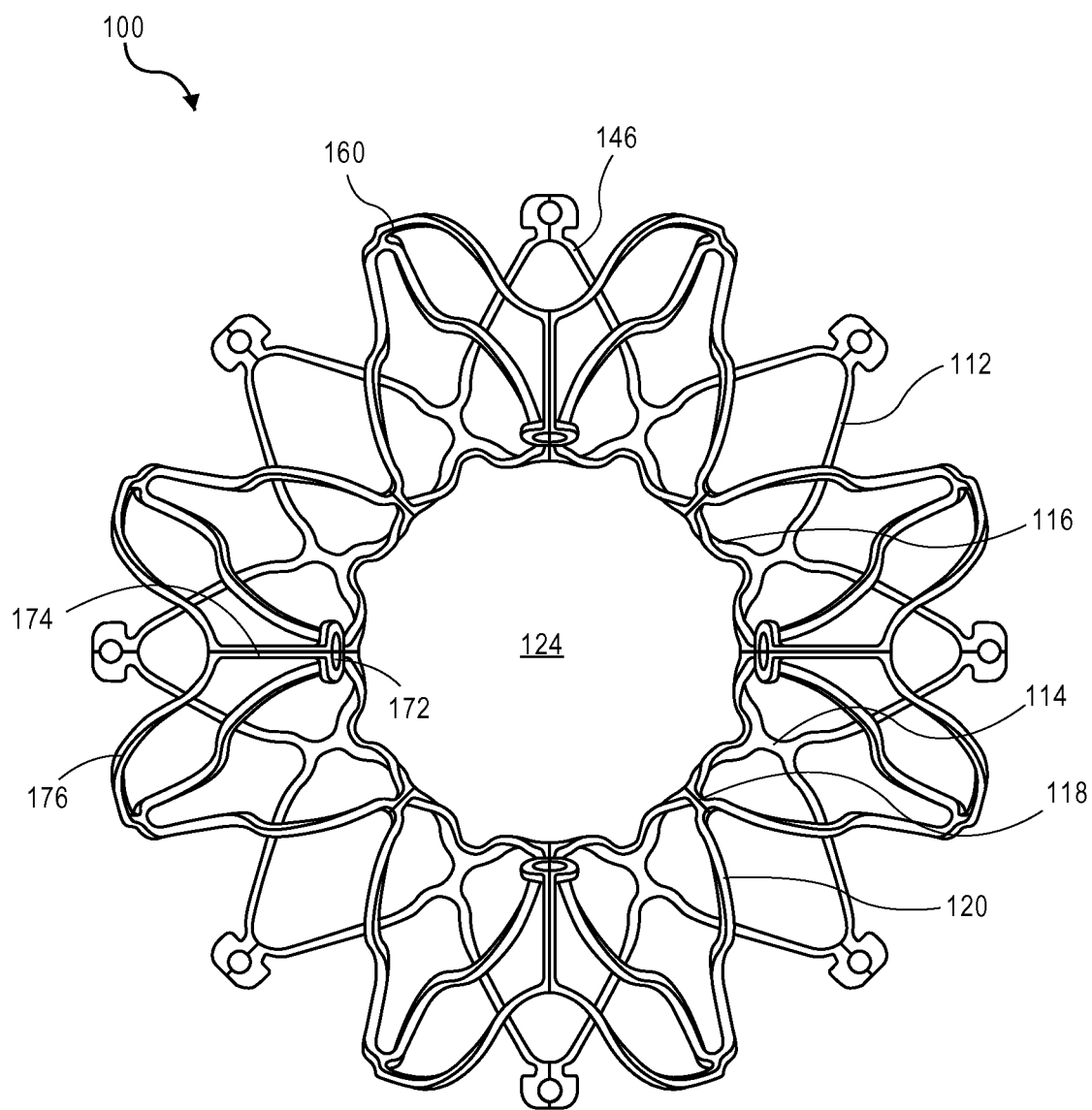
FIG. 7 is a top elevational view of a pressure regulating device according to another embodiment of this invention in a deployed configuration.
Figure 9:
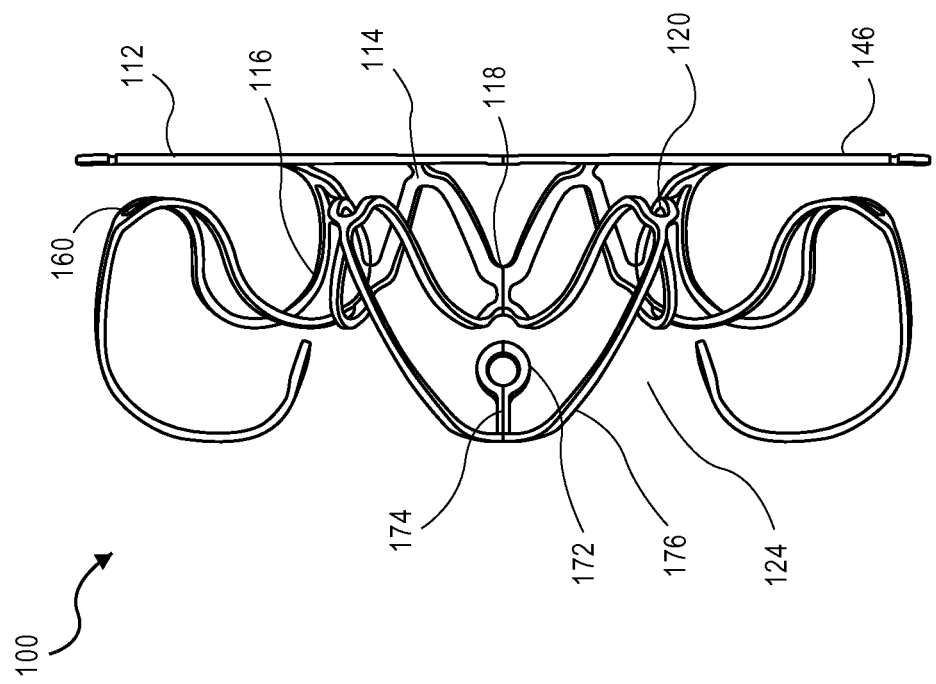
FIG. 9 is a perspective view of the device of FIG. 7 in the deployed configuration.
Figure 8:
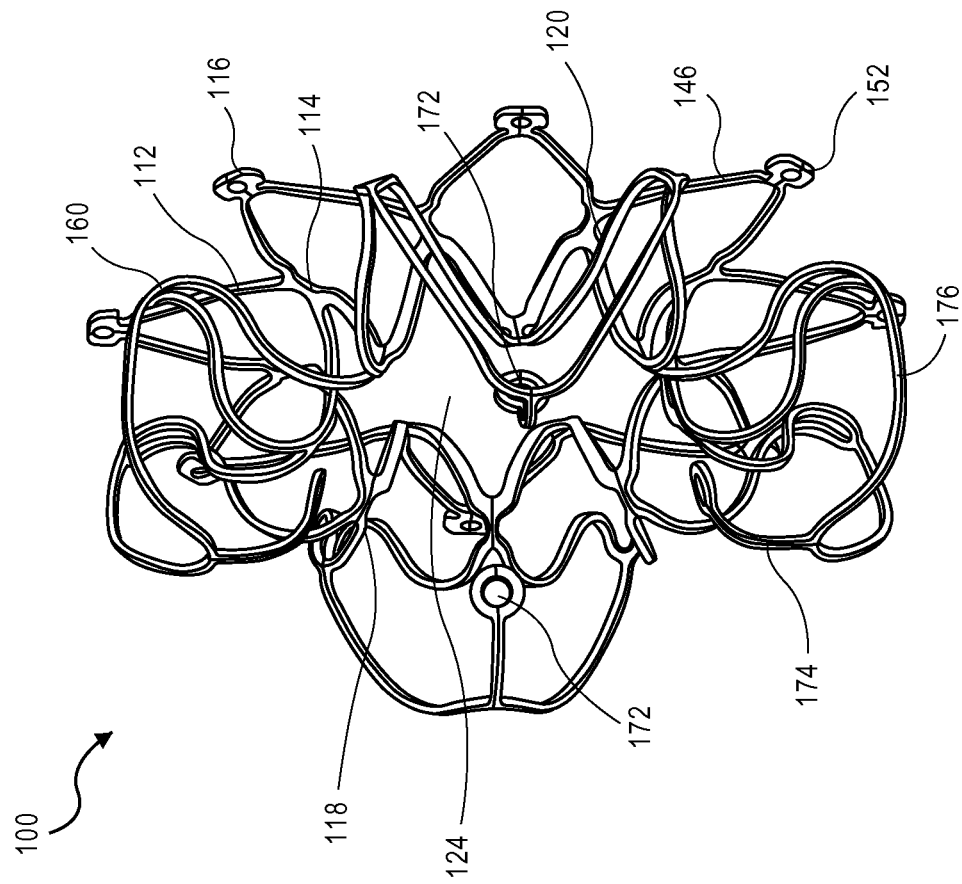
FIG. 8 is a side elevational view of the device of FIG. 7 in the deployed configuration.

FIGS. 7-13 illustrate another exemplary pressure regulating device 100 for, e.g., treating elevated left atrial pressure in a patient's heart. FIG. 7 is an end view of the deployed configuration of the device 100. FIG. 8 is an exemplary deployed configuration of the device 100. FIG. 9 is a side view of the deployed configuration of the device 100. FIG. 10 shows device 100 in a delivery configuration in which all portions of the device 100 are aligned in a generally linear profile and the retrieval attachment mechanisms overlap with each other. FIG. 11 is an illustrative view of a portion of the device 100 in flattened format solely for the purpose of showing various components of the device. Device 100 may be delivered via a delivery catheter (not shown) for deployment in the atrial septum of the patient's heart.

Similar to previously described embodiments, the device 100 includes a distal retention portion 112, a distal transition portion 114, a core region 116, a proximal transition portion 118, a proximal retention portion 120, and a proximal retrieval portion 122. Core region 116, distal transition struts 134, and distal retention portion 112, proximal transition portion 118, proximal retention portion 120, and secondary retrieval struts 176 and retrieval attachment mechanisms 172 shown in FIGS. 7-11, share some similarity to those illustrated with respect to the device 10 described in connection with FIGS. 1-6.

In the deployed configuration shown in FIGS. 7-9, the central core region 116 includes an opening 124 to permit blood to flow through the device from the left atrium to the right atrium. When in position in the patient's heart, the proximal retention region 120 has a plurality of flexible retention segments 160 that atraumatically engage the septal wall in the right atrium, and the distal retention region 112 has a plurality of flexible retention segments 146 that atraumatically engage the septal wall in the left atrium. In some embodiments, the proximal and distal retention regions may cooperate to apply a compressive force to the septal wall. In some embodiments, the proximal and distal retention regions do not apply a compressive force to the septal wall. In some embodiments, the core region may also apply a radially outward force on the portion of the septal wall through which it extends. In other embodiments, the core region does not apply a radially outward force on the portion of the septal wall through which it extends.

In some embodiments, the radial span of the distal retention region 112 in the deployed configuration may be the same as the radial span of the proximal retention region 120. In other embodiments, the radial span of the distal retention region 112 may be greater than the radial span of the proximal retention region to, e.g., account for the typically greater pressure in the left atrium compared to the pressure in the right atrium. In some embodiments, the distal retention region has a general diameter of 8-20 mm upon deployment. In another embodiment, the deployed proximal retention region has a general diameter of 8-20 mm upon deployment. According to some embodiments, upon deployment, the diameter of the deployed core region of the device is about 25-50% of the overall diameter of the deployed distal retention region.

The retrieval region 122 includes retrieval legs 174 extending proximally and radially inwardly from the radially outward ends of the proximal retention segments 160 via intermediate legs 176 disposed between the retrieval leg 174 and the proximal retention segments 160. According to some embodiments, each secondary retrieval leg 176 extends proximally from the proximal end of a proximal retention segment 160. As illustrated, a distal end of a secondary retrieval leg joins the proximal end of a proximal retention segment 160 where two adjacent proximal retention struts join. Loops or eyelets 172 at the ends of the retrieval legs 174 serve as connectors for the delivery and/or retrieval system. As shown in FIGS. 7-9, in the device's deployment configuration the eyelets 172 are proximal to and radially outward from the outer boundary of the opening 124 and therefore out of the path of any blood flowing through opening 124. In this embodiment, eyelets 172 are oriented in a plane generally parallel to the longitudinal axis of the core region 116.

FIG. 10 is a side view of device 100 in its collapsed delivery configuration. As shown, the radial dimensions of the proximal retention region 120, central core region 116 and distal retention region 112 are less in the delivery configuration than in the deployed configuration shown in FIGS. 7-9. The retrieval legs 174 and eyelets 172 extend proximally from the proximal retention region and connect to a delivery or retrieval system (not shown).

Figure 13:
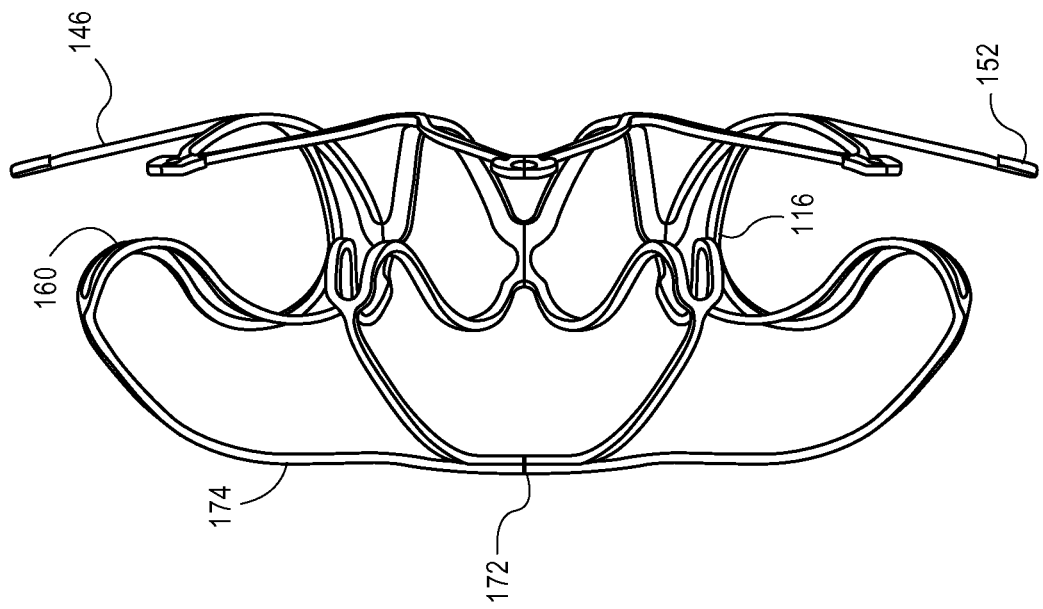
FIG. 13 is a side elevational view of the device of FIG. 7 in the retrieval configuration.
Figure 12:
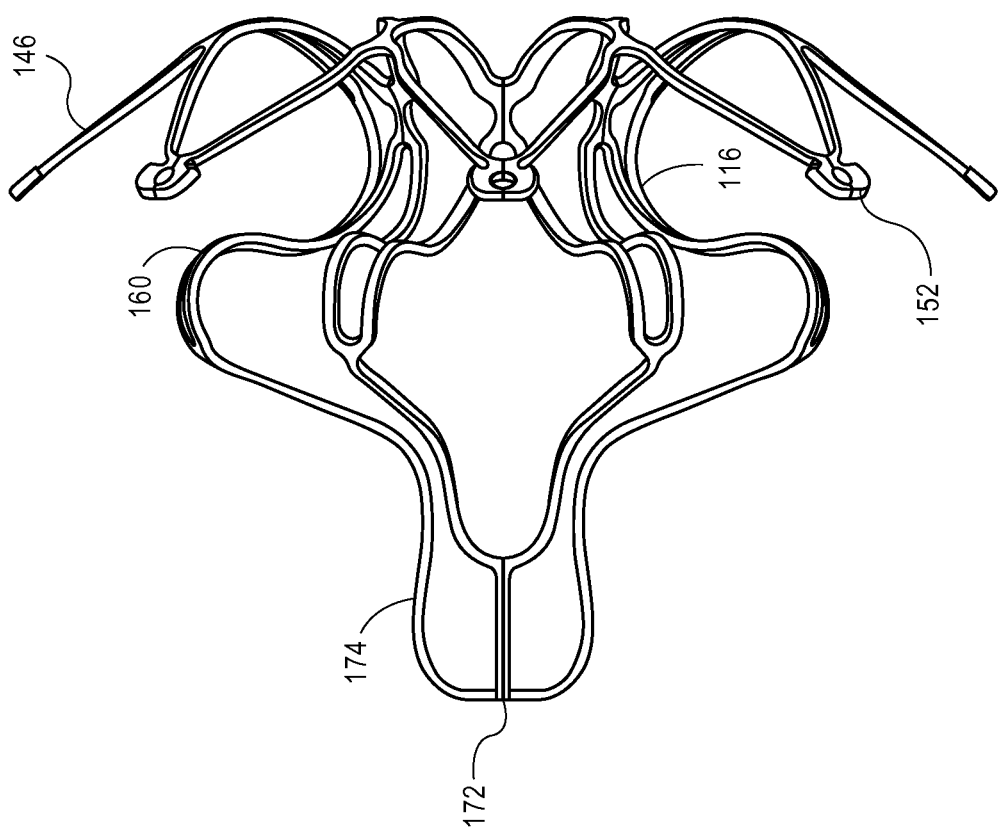
FIG. 12 is a side elevational view of the device of FIG. 7 transitioning from the delivery configuration to a retrieval configuration.

When deploying the device 100 into the septal wall, a delivery system advances device 100 through and out of a catheter. As it emerges from the catheter, the distal retention region 114 of device 100 begins to self-expand in the left atrium. Subsequently, the core region 116 and proximal retention region 120 expand as they emerge from the catheter in the septal wall opening and right atrium, respectively, while the eyelets 172 of the retrieval legs 174 are still connected to the delivery system. As shown in FIG. 12, distal retention segments 146, core region 116 and proximal retention segments 160 are substantially in their deployed configurations even while retrieval legs 174 extend proximally in an elongated profile into the delivery catheter (not shown) with the eyelets 172 overlapping each other and connected to a delivery system (not shown). In FIG. 13, retrieval legs 174 have emerged from the delivery catheter and have begun moving toward their expanded at-rest shapes; eyelets 172 are radially inward from their at-rest positions because they are still connected to the delivery system. This position is the retrieval configuration of device 100. After release from the delivery system, eyelets 172 move radially outward to their at-rest positions radially outside of the devices opening 124 (i.e., the deployed configuration shown in FIG. 7).

When retrieving device 100 for redeployment or removal, the retrieval device grasps eyelets 172, moving them radially inward. Device 100 is then pulled proximally into the retrieval catheter.

As in the earlier embodiments, portions of device 100 are arranged and configured to provide the desired bending behavior as device 100 emerges from and is drawn back into a delivery catheter, as shown in FIG. 11. Device 100 may be made with wavy patterns with hairpin turns, "V" shaped turns, open-cell or closed-cell designs. In some embodiments, as the core region transitions from its delivery configuration to its deployed configuration, the diameter of the core region increases and the core region reduces in length, sometimes slightly. In other embodiments, as the diameter of the core region increases, the overall length of the core region remains the same.

In some embodiments of the present teachings, the device 100 in its delivery configuration, such as illustrated in FIG. 10, is configured to be delivered and deployed through a 5 French-12 French catheter. In one embodiment, the elongated device 100 has a diameter ranging from about 1 mm to about 4 mm, and the central core region 116 in a deployed configuration has a diameter ranging from about 3 mm to about 12 mm, or from about 110% to about 300% of that of the core region 116 in its delivery configuration. In other embodiments, the struts of the shunt portion 116 have a width of about 0.005 inch to about 0.030 inch. In a delivery configuration, the gap between two adjacent portions of the core portion struts is from about 0" to about 0.010", and upon deployment, the gap between two adjacent portions of the struts is up to about 0.075".

In some embodiments of the present invention, the device 100 in its delivery configuration, such as illustrated in FIG. 10, has an overall length of about 5-25 mm, with the length of the core region 116 being 0.5-5 mm. In one embodiment, for a deployed device 100, the length of the core region 116 ranges from about 1 mm to about 7 mm, with the overall length of the device 100 ranging from about 3 mm to about 12 mm. In another embodiment, the length of the core region 116 of a deployed device ranges from about 30 to about 70% of the length of the device in the deployed profile.

According to some embodiments, as illustrated in FIG. 11, the bending location of device struts has a narrower width ("waist") than another portion, sometimes the remaining portions of the struts. In some embodiments, the lead-ins from both directions generally have a curved configuration. One skilled in the art should understand that although the bending location has curved lead-ins from both ends, other geometries, shapes, or profiles for narrowing the strut width at the bending location could also be used. Thus, what has been disclosed should not be viewed as limiting to the scope of the present teaching. In one embodiment, the waist has a width from about 0.003" to about 0.015", or from about 30% to about 110% of the width of the widest portion of the struts. Additionally, in order to control the bending direction, the width of the struts can be greater than the thickness. Additionally, the length of the distal transition portion, as well as the width of the waist could vary according to the overall size of the device and design criteria.

Upon deployment in vivo, the distal retention region 112 of device 100 is configured to be deployed inside the left atrium with each of the distal retention segments 146 located at the left atrial side of the atrial septum. In certain embodiments, the distal retention opposes the left atrial side of the atrial septum. According to some embodiments, upon deployment, the distal retention region 112 forms a disc-like configuration, with at least a portion, sometimes a substantial portion, of the surface area of each retention segment 146 contacting the atrial septum. In another embodiments, the distal retention region 112 forms an umbrella-like configuration with at least a portion, sometimes a substantial portion, of the surface area of each retention segment 146 doming away from the atrial septum. For example, one or more distal ends of the distal retention segments 146 can contact the atrial septum. In yet another embodiment, the distal retention region 112 forms a generally straight slope profile with at least a portion, sometimes a substantial portion, of the surface area of each distal retention segment 146 not contacting the atrial septum. In this particular embodiment, one or more distal ends of the distal retention segments 146 remain furthest away from the atrial septum. One skilled in the art should understand that other suitable profile could also be used. Thus the exemplary embodiments discussed, shown, or mentioned herein should not be viewed as limiting.

According to some embodiments, the distal ends of each distal retention segment 146 include a foot 152. The foot 152 is configured to prevent the distal ends of the distal retention segments 146 from penetrating, piercing, or eroding into the septal tissues. According to some embodiments, the foot is configured to provide a larger surface area for contacting the tissues and/or reducing the force that the distal retention segments 146 apply onto the tissues. In some embodiments, the foot 152 is also configured to incorporate a radiopaque marker.

When the device 100 is at its delivery configuration, the proximal transition portion 118 has a small generally tubular profile, such as illustrated in FIG. 10, with adjacent struts packed closely and parallel to each other. The proximal transition portion 118 is also configured to transform from a delivery configuration to a deployed configuration. During such transition, a proximal section of the struts extends radially outwardly, and a distal section of the struts expands as the core region 116 expands radially into its deployed configuration. Thus, while the device 100 is in its deployed configuration, the proximal transition struts bend at a location so that the core region 116 of the device has a tubular profile at the distal end of the proximal transition struts, and the proximal retention region 120 of the device 100 have a radially outward umbrella-shaped profile that is generally at an angle, sometimes perpendicular, to the longitudinal axis of the core region 116 at the proximal end of the proximal transition struts.

According to some embodiments, as illustrated in FIG. 11, the bending location on the proximal transition struts has a narrower width ("waist") than another portion, sometimes the remaining portions, of the struts. In some embodiments, the lead-ins from both direction have a generally curved configuration. One skilled in the art should understand that although the bending location has a generally curved led-ins from both ends of the waist, other geometries, shapes, or profiles for narrowing the strut width at the bending location could also be used. Thus what has been disclosed should not be viewed as limiting. In one embodiment, the waist has a width from about 0.006" to about 0.030", or from about 25 to about 80% of the width of the widest portion of the proximal transition struts. In addition, in order to control the bending direction, the width of the proximal transition struts can be greater than the thickness of the proximal transition struts. Additionally, in some embodiments, the proximal transition struts are shorter and narrower than the distal transition struts of the device. One skilled in the art should understand that the proximal transition struts can have the same length and/or width as the distal transition struts.

Similar to the distal retention region 112, the device 100 can also have a proximal retention region 120. In some embodiments, the proximal retention region 120 of the device 100 has an expanded umbrella-like profile when deployed, as illustrated in FIG. 7, and a collapsed generally tubular profile during delivery, as illustrated in FIG. 10. The proximal retention region 120 includes multiple proximal retention segments 160. In various embodiments, each of the proximal retention segments is formed by two adjacent proximal retention struts extending proximally from the proximal end of a proximal transition strut. The distal ends of the two proximal retention struts are located side by side from each other with a gap in between. According to one embodiment, the distal ends of two proximal retention struts extend from the proximal end of two adjacent proximal transition struts to connect to each other, forming a proximal retention segment 160. According to some embodiments, in a delivery configuration, the proximal retention segment 160 formed by two adjacent proximal retention struts are relatively elongated with two adjacent proximal retention struts extending close to each other; and in deployed configuration, the proximal retention segment 160 formed by two adjacent proximal retention struts are expanded in width and shortened in the overall length with the gap between two adjacent proximal retention struts widened.

According to one embodiment, when the device 100 is in its delivery configuration, the proximal retention portion 120 radially collapses with the proximal retention segments 160 orienting longitudinally along the longitudinal axis of the core region 116, and when the device 100 is in its deployed configuration, the proximal retention portion 120 radially expands with the proximal retention segment 160 curving distally. When the device is deployed in vivo, according to some embodiments, for example as illustrated in FIG. 9, a first section of each proximal retention segment 160 curves distally toward the atrial septum forming a first curve, a second section of each proximal retention segment 160 curves proximally away from the atrial septum forming a second curve, with a portion of each proximal retention segment 160 between the first and second sections of each proximal retention segment 160 contacting the septal tissue.

The curved deployment configuration of the proximal retention region 120 allows the device to accommodate various atrial septum thickness. For example, for a thin atrial septum, the curved proximal retention segments 160 can fully assume its pre-defined curved deployment configuration. For a thick atrial septum, the curved proximal retention segments 160 can oppose the atrial septum, and when the septum pushes back, the curved proximal retention segments 160 can deflect at their first curve while maintaining the device 100 in place.

According to some embodiments, curving the second section of the deployed proximal retention region 120 away from the atrial septum enlarges the contacting surface area with the septal tissue, thereby preventing any trauma to the tissue. One skilled in the art should understand, the second curve of the proximal retention segments 160 can start at any location near or at the proximal ends of each retention segment 160.

According to some embodiments, in a delivery configuration, the proximal retention region struts have a similar width as the distal retention struts. In other embodiments, the proximal retention struts have a different width than the distal retention struts. In yet another embodiment, the width of the strut of the core region 116 is greater than that of the proximal retention struts and that of the distal retention struts, so that the core region 116 is more rigid than the proximal and distal retention portions 112, 120. According to one embodiment of the present teachings, upon deployment, the stiff core region 116 pushes the surrounding tissue radially outwardly, thereby maintaining the size of the opening for the treatment, while the relative pliable proximal and distal retention portions 112, 120 gently contact the septal tissue without penetration.

According to some embodiments, at least some of the proximal retention struts are longer than some of the distal retention struts. In some embodiments, all of the proximal retention struts are longer than the distal retention struts. In some embodiments, the distal retention struts have a length of about 2-7 mm. In some embodiments, the proximal retention struts have a length of about 2-14 mm. One skilled in the art should understand that the specific length of the distal retention struts and/or proximal retention struts should be determined by, inter alia, the overall size of the device, which in turn is determined by the needs of a patient. According to some embodiments, the proximal retention struts are configured so that, upon full deployment, its first section curves toward the septum, forming a space between a portion of the strut and septum, and the most radially outward portion of the proximal retention struts is at or near the most radially outward portion of the distal retention struts on the opposite side of the septum.

In various embodiments, the device 100 is fabricated from a tube. Thus, all portions of the device 100, such as the distal retention portion 112, the distal transitional portion 114, the central core region 116, the proximal transitional portion 118, the proximal retention portion 120, and proximal retrieval portion 122, have a same thickness. In one embodiment, the thickness of the tube, and thus the thickness of each portion of the device, is from 0.005-0.007 inch. In another embodiment, at least one portion of the device 100 has a different thickness than the rest of the device. This, in some circumstances, can be achieved by removing material from other portions.

In one embodiment, the width of each portion, such as the distal retention portion 112, the distal transitional portion 114, the core region 116, the proximal transitional portion 118, the proximal retention portion 120, and proximal retrieval portion 122, of the device 100 is the same as the thickness of the portion. In another embodiment, the width of the distal retention portion 112, the distal transitional portion 114, the core region 116, the proximal transitional portion 118, and the proximal retention portion 120, are greater than the thickness of these portions. In some embodiments, the width of the proximal retrieval portion 122 is the same as the thickness. According to some embodiments, for portions of the device having a width greater than the thickness, the curving and bending of such portions can be achieved in a controlled manner, without risking the struts being twisted during the process. For other portions of the device where twisting is expected, or less concerning, such as the proximal retrieval portion, the thickness and width can be the same. According to some embodiments, the thickness of each portion of the device ranges from about 0.003" to about 0.09".

According to some embodiments, the retrieval eyelets 172 are configured to be attached to a flexible delivery mechanism. In one embodiment (not shown), a delivery filament, such as a wire or a suture, extends through one or more retrieval attachment mechanisms with both ends of the filament being controlled by a clinician. Upon deployment, one end of the delivery filament is loosened and the other end of the delivery filament is retracted proximally so that the entire flexible delivery filament is removed from the body. One skilled in the art would understand that a flexible delivery filament allows the device fully deploy at a treatment location, while still under the control of the clinician, so that the deployment can be assessed and the device can be retrieved if necessary.

According to some embodiments, the retrieval eyelets 172 are configured to be attached to a relatively rigid delivery mechanism. In one embodiment (not shown), a delivery shaft with notches at its distal end for hosting the retrieval eyelets 172. During delivery, the retrieval eyelets 172 is secured inside the notch, and upon deployment, the retrieval eyelets 172 are released from the notch. One skilled in the art would understand that a relatively rigid delivery shaft can push the device distally inside the delivery catheter and to deploy device.

According to one embodiment of the present teachings, the device 100 is pre-set into its deployed profile and stretched into an elongated profile, such as shown in FIG. 10, for percutaneous delivery. Upon deployment, the device will recover to its pre-set deployed configuration once free from constraint of the delivery catheter. To minimize any deformation during the delivery process, according to one embodiment of the present teachings, the maximum ratio of the thickness (t) of a curved portion of the device (e.g., the transition from proximal retention segments 60 to secondary retrieval legs 76) over two times of the radius "R" of that curved portion is 0.12, i.e., $t/2R \leq 12\%$. Maintaining this ratio will ensure the maximum recovery of the intended curvature.

Figure 15:
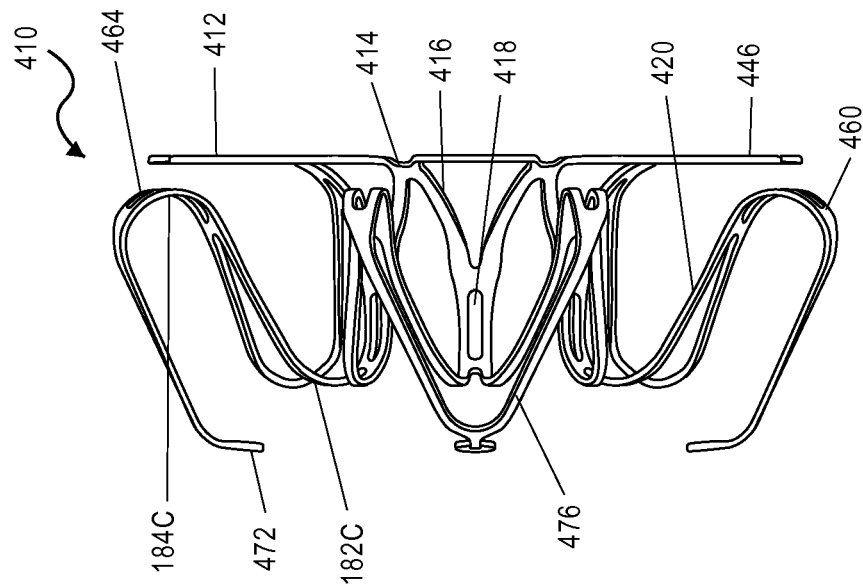
FIG. 15 is a side elevational view of the device of FIG. 14 in the deployed configuration.
Figure 14:
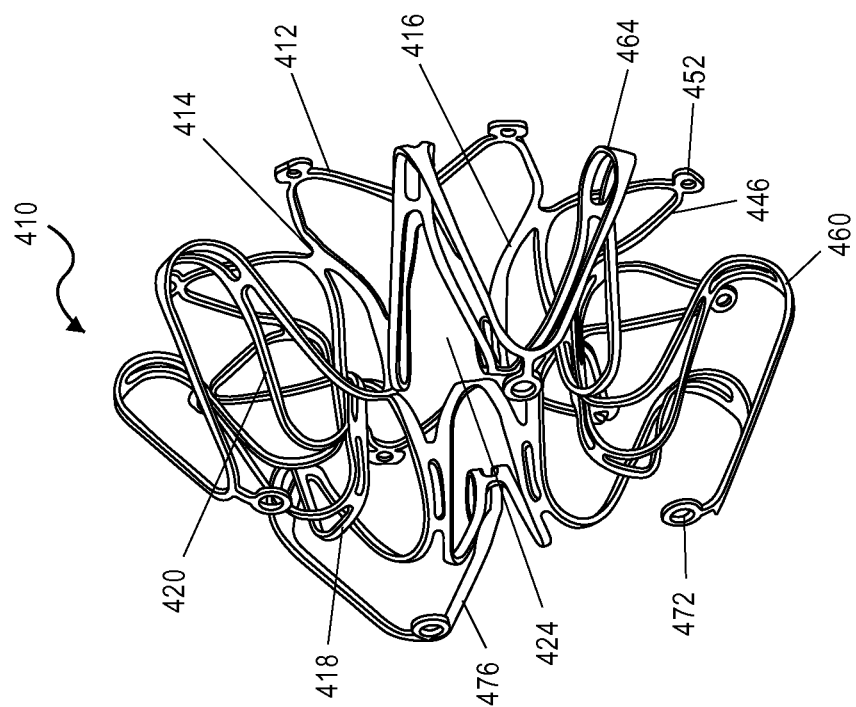
FIG. 14 is a perspective view of a pressure regulating device according to yet another embodiment of the invention in a deployed configuration.
Figure 16:
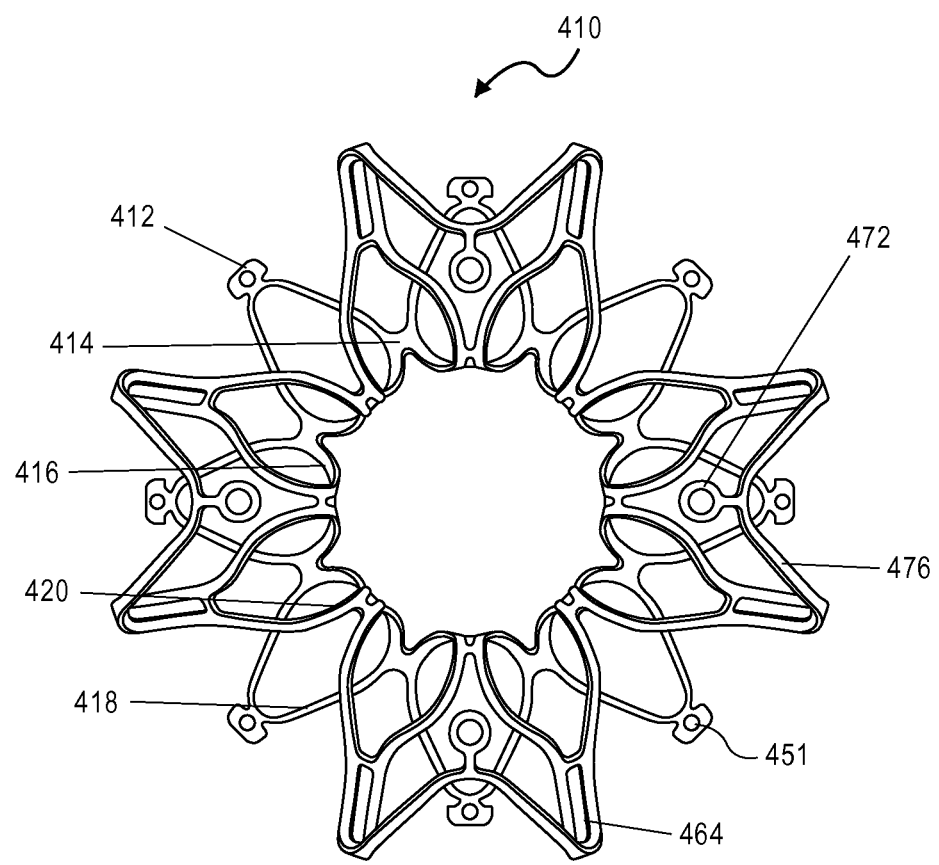
FIG. 16 is a top elevational view of the device of FIG. 14 in the deployed configuration.

FIGS. 14-17 show another embodiment of a pressure regulating device 410 for, e.g., treating elevated left atrial pressure in a patient's heart according to this invention. FIGS. 14-16 show the device 410 in a deployed configuration. In its delivery configuration (not shown), device 410 is collapsed into a generally tube-like configuration, such as shown in FIGS. 3 and 10 with respect to embodiments discussed above. A distal retention region 412 extends distally from a central core region 416 via a distal transition region 414, and a proximal retention region 420 extends proximally from core region 416 via a proximal transition region 418. As shown in this figure, the proximal transition portion 418 has a relatively longer overall length, and greater overall width, than prior embodiments. Thus, in order to reduce the mass of the struts, as well as reducing the size of the delivery profile, the geometrical center of the strut is hollowed out resulting a two adjacent struts 452, 454 in between the distal and proximal ends of the proximal transition portion 418.

In the delivery configuration (not shown), device 410 (including distal retention region 412, central core region 416 and proximal retention region 420) is radially compressed and axially elongated compared to the deployed configuration shown in FIGS. 14-16. Device 410 may be delivered via a delivery catheter (not shown) for deployment in the atrial septum of the patient's heart.

In the deployed configuration shown in FIGS. 14-16, the central core region 416 includes an opening 424 to permit blood to flow through the device from the left atrium to the right atrium. When in position in the patient's heart, the radially expanded proximal retention region 420 has a plurality of flexible retention segments 460 that atraumatically engage the septal wall in the right atrium, and the radially expanded distal retention region 412 has a plurality of flexible retention segments 446 that atraumatically engage the septal wall in the left atrium. In some embodiments, the proximal and distal retention regions may cooperate to apply a compressive force to the septal wall. In some embodiments, the proximal and distal retention regions do not apply a compressive force to the septal wall. In some embodiments, the core region may also apply a radially outward force on the portion of the septal wall through which it extends. In other embodiments, the core region does not apply a radially outward force on the portion of the septal wall through which it extends.

In some embodiments, the radial span of the distal retention region 412 in the deployed configuration may be the same as the radial span of the proximal retention region 420. In other embodiments, the radial span of the distal retention region 412 may be greater than the radial span of the proximal retention region to, e.g., account for the typically greater pressure in the left atrium compared to the pressure in the right atrium. In some embodiments, the distal retention region has a general diameter of 8-20 mm upon deployment. In another embodiment, the deployed proximal retention region has a general diameter of 8-20 mm upon deployment. According to some embodiments, upon deployment, the diameter of the deployed core region of the device is about 25-50% of the overall diameter of the deployed distal retention region.

Figure 17:
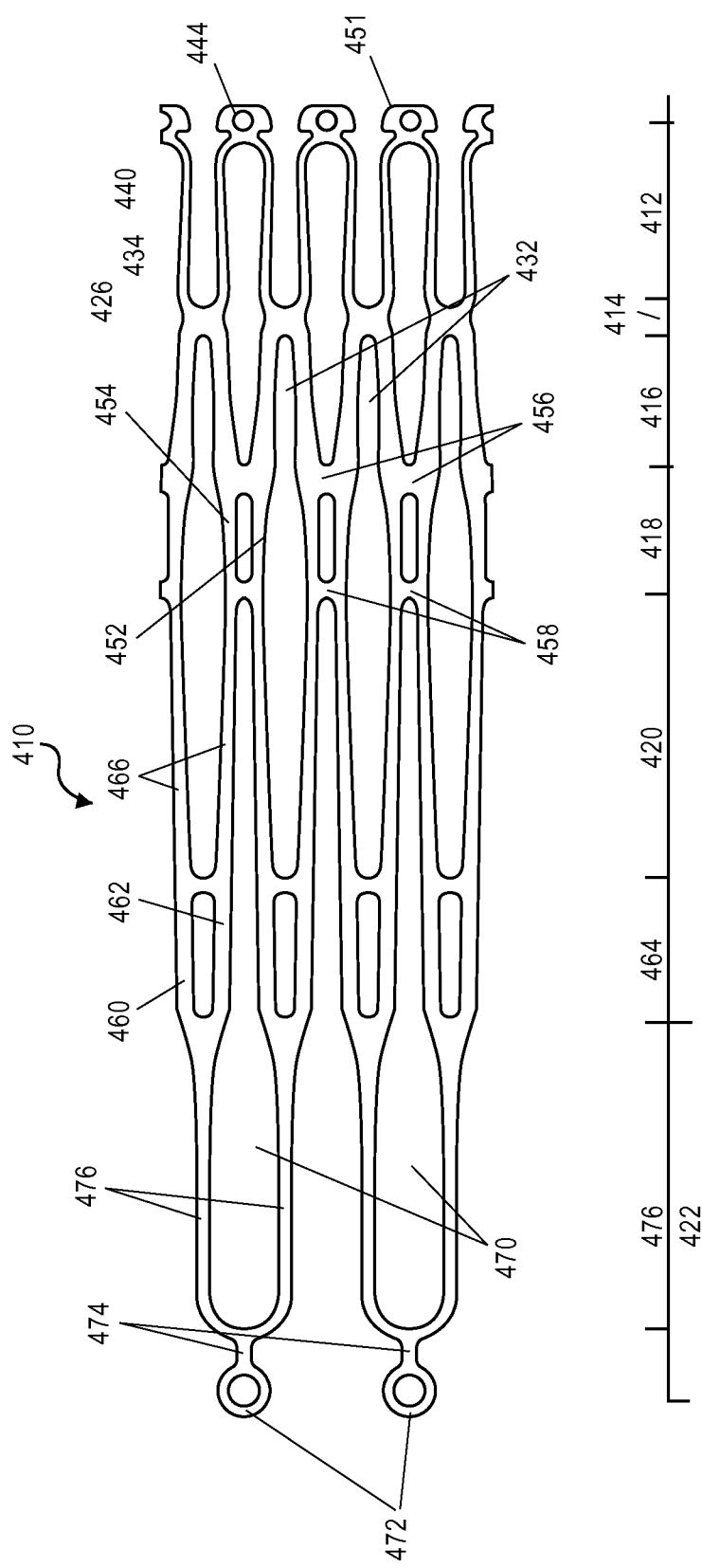
FIG. 17 is a flattened view of a portion of the device of FIG. 14.

The retrieval region 422 includes retrieval legs 474 extending proximally and radially inwardly from the radially outward ends of the proximal retention segments 460, optionally via intermediate legs 476 disposed between the retrieval legs 474 and a junction 464, and the proximal retention segments 460. As illustrated in FIG. 17, junction 464 has a relatively greater overall length and greater overall width. Similar to proximal transition portion 418, in order to reduce the mass of the junction 464, as well as reducing the size of the delivery profile, geometrical center of the junction 464 is hollowed out resulting a two adjacent struts 462, 460 in between the distal and proximal ends of the junction 464. Loops or eyelets 472 at the proximal ends of the retrieval legs 474 serve as connectors for the delivery and/or retrieval system. As shown in FIGS. 14-16, in the device's deployed configuration the eyelets 472 are proximal to and radially outward from the outer boundary of the opening 424 and therefore out of the path of any blood flowing through opening 424. In this embodiment, eyelets 472 are oriented in a plane generally perpendicular to the longitudinal axis of the core region 416.

When deploying the device 410 into the septal wall, a delivery system advances device 410 through and out of a catheter. As it emerges from the catheter, the distal retention region 414 of device 410 begins to self-expand in the left atrium. Subsequently, the core region 416 and proximal retention region 420 expand as they emerge from the catheter in the septal wall opening and right atrium, respectively, all while the eyelets 472 of the retrieval legs 474 are still connected to the delivery system. Distal retention segments 446, core region 416 and proximal retention segments 460 are substantially in their deployed configurations even while retrieval legs 474 and 476 extend proximally into the delivery catheter (not shown). After they emerge from the delivery catheter, retrieval legs 474 and 476 begin moving toward their expanded at-rest shapes, while eyelets 472 remain radially inward (in the device's retrieval configuration) from their at-rest positions because they are still connected to the delivery system. After release from the delivery system, eyelets 472 move radially outward to their at-rest positions radially outside of the device's opening 424 (i.e., the deployed configuration shown in FIG. 16).

When retrieving device 410 for redeployment or removal, the retrieval device grasps eyelets 472, moving them radially inward. Device 410 is then pulled proximally into the retrieval catheter.

As in the earlier embodiments, portions of device 410 are arranged and configured to provide the desired bending behavior as device 410 emerges from and is drawn back into a delivery catheter, as shown in FIG. 17. Device 410 may be made with wavy patterns with hairpin turns, "V" shaped turns, open-cell or closed-cell designs. In some embodiments, as the core region transitions from its delivery configuration to its deployed configuration, the diameter of the core region increases and the core region reduces in length, sometimes slightly. In other embodiments, as the diameter of the core region increases, the overall length of the core region remains the same.

In some embodiments of the present teachings, the device 410 in its delivery configuration is configured to be delivered and deployed through a 5 French-12 French catheter. In one embodiment, the elongated device 410 has a diameter ranging from about 1 mm to about 4 mm, and the central core region 416 in a deployed configuration has a diameter ranging from about 3 mm to about 12 mm, or from about 110% to about 300% of that of the core region 416 in its delivery configuration. In other embodiments, the struts of the shunt portion 416 have a width of about 0.005 inch to about 0.030 inch. In a delivery configuration, the gap between two adjacent portions of the core portion struts is from about 0" to about 0.010", and upon deployment, the gap between two adjacent portions of the struts is up to about 0.075".

In some embodiments of the present invention, the device 410 in its delivery configuration has an overall length of about 5-25 mm, with the length of the core region 416 being 0.5-5 mm. In one embodiment, for a deployed device 410, the length of the core region 416 ranges from about 1 mm to about 7 mm, with the overall length of the device 410 ranging from about 3 mm to about 12 mm. In another embodiment, the length of the core region 416 of a deployed device ranges from about 30 to about 70% of the length of the device in the deployed profile.

According to some embodiments, as illustrated in FIG. 17, the bending location of distal transition region 414 has a narrower width ("waist") than another portion, sometimes the remaining portions of the struts. In some embodiments, the lead-ins from both directions generally have a curved configuration. One skilled in the art should understand that although the bending location has curved lead-ins from both ends, other geometries, shapes, or profiles for narrowing the strut width at the bending location could also be used. Thus, what has been disclosed should not be viewed as limiting to the scope of the present teaching. In one embodiment, the waist has a width from about 0.003" to about 0.015", or from about 30% to about 110% of the width of the widest portion of the struts. Additionally, in order to control the bending direction, the width of the struts can be greater than the thickness. Additionally, the length of the distal transition portion, as well as the width of the waist could vary according to the overall size of the device and design criteria.

Upon deployment in vivo, the distal retention region 412 of device 410 is configured to be deployed inside the left atrium with each of the distal retention segments 446 located at the left atrial side of the atrial septum. In certain embodiments, the distal retention opposes the left atrial side of the atrial septum. According to some embodiments, upon deployment, the distal retention region 412 forms a disc-like configuration, with at least a portion, sometimes a substantial portion, of the surface area of each retention segment 446 contacting the atrial septum. In another embodiments, the distal retention region 412 forms an umbrella-like configuration with at least a portion, sometimes a substantial portion, of the surface area of each retention segment 446 doming away from the atrial septum. For example, one or more distal ends of the distal retention segments 446 can contact the atrial septum. In yet another embodiment, the distal retention region 412 forms a generally straight slope profile with at least a portion, sometimes a substantial portion, of the surface area of each distal retention segment 446 not contacting the atrial septum. In this particular embodiment, one or more distal ends of the distal retention segments 446 remain furthest away from the atrial septum. One skilled in the art should understand that other suitable profile could also be used. Thus the exemplary embodiments discussed, shown, or mentioned herein should not be viewed as limiting.

According to some embodiments, the distal ends of each distal retention segment 446 include a foot 451. The foot 451 is configured to prevent the distal ends of the distal retention segments 446 from penetrating, piercing, or eroding into the septal tissues. According to some embodiments, the foot is configured to provide a larger surface area for contacting the tissues and/or reducing the force that the distal retention segments 446 apply onto the tissues. In some embodiments, the foot 451 is also configured to incorporate a radiopaque marker.

When the device 410 is at its delivery configuration, the proximal transition portion 418 has a small generally tubular profile, with adjacent struts packed closely and parallel to each other. The proximal transition portion 418 is also configured to transform from a delivery configuration to a deployed configuration. During such transition, a proximal section of the struts extends radially outwardly, and a distal section of the struts expands as the core region 416 expands radially into its deployed configuration. Thus, while the device 410 is in its deployed configuration, the proximal transition struts bend at a location so that the core region 416 of the device has a tubular profile at the distal end of the proximal transition struts, and the proximal retention region 420 of the device 410 have a radially outward umbrella-shaped profile that is generally at an angle, sometimes perpendicular, to the longitudinal axis of the core region 416 at the proximal end of the proximal transition struts.

Similar to the distal retention region 412, the device 410 can also have a proximal retention region 420. In some embodiments, the proximal retention region 420 of the device 410 has an expanded umbrella-like profile when deployed, as illustrated in FIGS. 14-16, and a collapsed generally tubular profile during delivery. The proximal retention region 420 includes multiple proximal retention segments 460. In various embodiments, each of the proximal retention segments is formed by two adjacent proximal retention struts extending proximally from the proximal end of a proximal transition strut. The distal ends of the two proximal retention struts are located side by side from each other with a gap in between. According to one embodiment, the distal ends of two proximal retention struts extend from the proximal end of two adjacent proximal transition struts to connect to each other, forming a proximal retention segment 460. According to some embodiments, in a delivery configuration, the proximal retention segment 460 formed by two adjacent proximal retention struts are relatively elongated with two adjacent proximal retention struts extending close to each other; and in deployed configuration, the proximal retention segment 460 formed by two adjacent proximal retention struts are expanded in width and shortened in the overall length with the gap between two adjacent proximal retention struts widened.

According to one embodiment, when the device 410 is in its delivery configuration, the proximal retention portion 420 radially collapses with the proximal retention segments 460 orienting longitudinally along the longitudinal axis of the core region 416, and when the device 410 is in its deployed configuration, the proximal retention portion 420 radially expands with the proximal retention segment 460 curving distally. When the device is deployed in vivo, according to some embodiments, for example as illustrated in FIG. 15, a first section of each proximal retention segment 460 curves distally toward the atrial septum forming a first curve, a second section of each proximal retention segment 460 curves proximally away from the atrial septum forming a second curve, with a portion of each proximal retention segment 460 between the first and second sections of each proximal retention segment 460 contacting the septal tissue.

The curved deployment configuration of the proximal retention region 420 allows the device to accommodate various atrial septum thickness. For example, for a thin atrial septum, the curved proximal retention segments 460 can fully assume its pre-defined curved deployment configuration. For a thick atrial septum, the curved proximal retention segments 460 can oppose the atrial septum, and when the septum pushes back, the curved proximal retention segments 460 can deflect at their first curve while maintaining the device 410 in place.

According to some embodiments, curving the second section of the deployed proximal retention region 420 away from the atrial septum enlarges the contacting surface area with the septal tissue, thereby preventing any trauma to the tissue. One skilled in the art should understand, the second curve of the proximal retention segments 460 can start at any location near or at the proximal ends of each retention segment 460.

According to some embodiments, in a delivery configuration, the proximal retention region struts have a similar width as the distal retention struts. In other embodiments, the proximal retention struts have a different width than the distal retention struts. In yet another embodiment, the width of the strut of the core region 416 is greater than that of the proximal retention struts and that of the distal retention struts, so that the core region 416 is more rigid than the proximal and distal retention portions 412, 420. According to one embodiment of the present teachings, upon deployment, the stiff core region 416 pushes the surrounding tissue radially outwardly, thereby maintaining the size of the opening for the treatment, while the relative pliable proximal and distal retention portions 412, 420 gently contact the septal tissue without penetration.

According to some embodiments, at least some of the proximal retention struts are longer than some of the distal retention struts. In some embodiments, all of the proximal retention struts are longer than the distal retention struts. In some embodiments, the distal retention struts have a length of about 2-7 mm. In some embodiments, the proximal retention struts have a length of about 2-14 mm. One skilled in the art should understand that the specific length of the distal retention struts and/or proximal retention struts should be determined by, inter alia, the overall size of the device, which in turn is determined by the needs of a patient. According to some embodiments, the proximal retention struts are configured so that, upon full deployment, its first section curves toward the septum, forming a space between a portion of the strut and septum, and the most radially outward portion of the proximal retention struts is at or near the most radially outward portion of the distal retention struts on the opposite side of the septum.

In various embodiments, the device 410 is fabricated from a tube. Thus, all portions of the device 410, such as the distal retention portion 412, the distal transitional portion 414, the central core region 416, the proximal transitional portion 418, the proximal retention portion 420, and proximal retrieval portion 422, have a same thickness. In one embodiment, the thickness of the tube, and thus the thickness of each portion of the device, is from 0.005-0.007 inch. In another embodiment, at least one portion of the device 410 has a different thickness than the rest of the device. This, in some circumstances, can be achieved by removing material from other portions.

In one embodiment, the width of the distal retention portion 412, the distal transitional portion 414, the core region 416, the proximal transitional portion 418, and the proximal retention portion 420, are greater than the thickness of these portions. In some embodiments, the width of the proximal retrieval portion 422 is the same as the thickness. According to some embodiments, for portions of the device having a width greater than the thickness, the curving and bending of such portions can be achieved in a controlled manner, without risking the struts being twisted during the process. For other portions of the device where twisting is expected, or less concerning, such as the proximal retrieval portion, the thickness and width can be the same. According to some embodiments, the thickness of each portion of the device ranges from about 0.003" to about 0.09".

According to some embodiments, the retrieval eyelets 472 are configured to be attached to a flexible delivery mechanism. In one embodiment (not shown), a delivery filament, such as a wire or a suture, extends through one or more retrieval attachment mechanisms with both ends of the filament being controlled by a clinician. Upon deployment, one end of the delivery filament is loosened and the other end of the delivery filament is retracted proximally so that the entire flexible delivery filament is removed from the body. One skilled in the art would understand that a flexible delivery filament allows the device fully deploy at a treatment location, while still under the control of the clinician, so that the deployment can be assessed and the device can be retrieved if necessary.

According to some embodiments, the retrieval eyelets 472 are configured to be attached to a relatively rigid delivery mechanism. In one embodiment (not shown), a delivery shaft with notches at its distal end for hosting the retrieval eyelets 472. During delivery, the retrieval eyelets 472 is secured inside the notch, and upon deployment, the retrieval eyelets 472 are released from the notch. One skilled in the art would understand that a relatively rigid delivery shaft can push the device distally inside the delivery catheter and to deploy device.

According to one embodiment of the present teachings, the device 410 is pre-set into its deployed profile and stretched into an elongated profile for percutaneous delivery. Upon deployment, the device will recover to its pre-set deployed configuration once free from constraint of the delivery catheter. To minimize any deformation during the delivery process, according to one embodiment of the present teachings, the maximum ratio of the thickness (t) of a curved portion of the device (e.g., the transition from proximal retention segments 460 to secondary retrieval legs 476) over two times of the radius "R" of the curved portion is 0.12, i.e., $t/2R \leq 12\%$. Maintaining this ratio will ensure the maximum recovery of the intended curvature.

Figure 19:
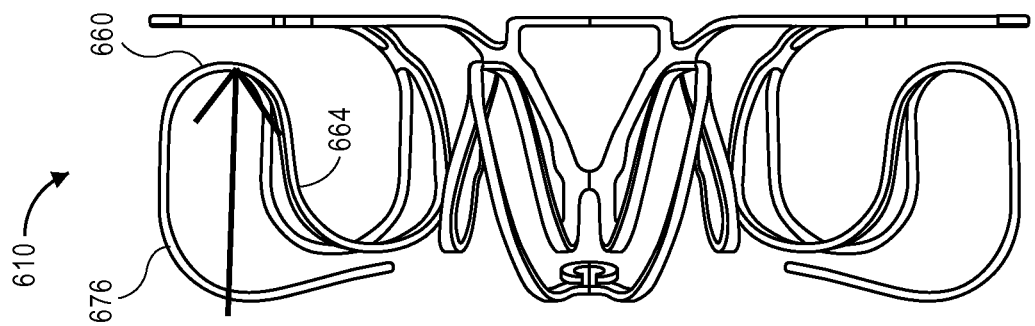
FIG. 19 is a side elevational view of a pressure regulating device according to another embodiment of the invention.
Figure 18:
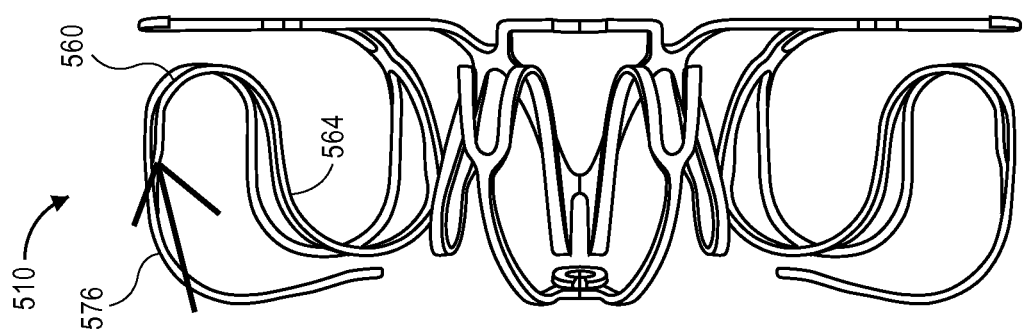
FIG. 18 is a side elevational view of a pressure regulating device according to still another embodiment of the invention.

The attachment points of between the elements forming the proximal retention region and the retrieval legs may affect the behavior of the device during deployment and retrieval. FIGS. 18 and 19 illustrate two different configurations. In device 510 shown in FIG. 18, struts 564 forming proximal retention segment 560 meet retrieval strut 576 proximal to curve between the tissue contact surface of retention segment 560 and strut 576, as shown by the arrow in FIG. 18. By contrast, in FIG. 19, struts 664 forming proximal retention segment 660 meet retrieval strut 676 at the tissue contact surface of retention segment 660, as shown by the arrow in FIG. 19. Device 510 shown in FIG. 18 is less likely to twist during retrieval than the device 610 shown in FIG. 19 due at least in part to the different locations of these connection points.

According to one embodiment, the device of the present teachings is manufactured by laser cutting a biocompatible metal tube. According to some embodiments, the device is made of a biocompatible metal or polymer. In various embodiments, the entire device is made of a biocompatible metal or polymer. In some embodiments, the device in its entirely or portion(s) thereof, for example, those with curved/bent deployment configuration, is made of an elastic material, a super-elastic material, or a shape-memory alloy so that the above portions can be distorted into a generally straightened profile during the delivery process and resume and maintain its intended profile in vivo once it is deployed from a delivery catheter. In some embodiments, the device is made of stainless steel, nitinol, Titanium, Elgiloy, Vitalium, Mobilium, Ticonium, Platinore, Stellite, Tantalum, Platium, Hastelloy, CoCrNi alloys (e.g., trade name Phynox), MP35N, or CoCrMo alloys, any other metallic alloys, or a mixture thereof. Alternatively, in some embodiments, a part of the device or the entire device is made of a polymer, such as PTFE, UHMPE, HDPE, polypropylene, polysulfone, or other biocompatible plastic. The surface finish of the device can be textured to induce tissue response and tissue in-growth for improved stabilization. Alternatively, a part of or the entirely of the device can be fabricated from a resorbable polymer. In some embodiments, the resorbable polymer includes polyactic acid, polyglycolic acid, polycaprolactone, a combination of two or more of the above or a variety of other resorbable polymers that are well known to those skilled in the art.

According to one embodiment of the present teachings, the device is fabricated from a tubular form and then shaped to its final configuration. In one embodiment, if a sufficiently elastic and resilient material, such as nitinol, is used, the structure is preformed into the finished shape and elastically deformed. In some embodiments, the device is stowed in a delivery device during the delivery and the device elastically recovers its shape upon deployment. In some embodiments, one, some, or all portions of the device are manually expanded to the desired diameter and/or curved to a pre-set shape. In certain embodiment, one, some, or all portions of the device is heat set in an oven while constrained to the desired shape.

According to one embodiment of the present teachings, at least one portion of the device expands radially upon being deployed in vivo. According to one embodiment of the present teachings, upon deployment, the radial expansion of at least one portion of the device is due to the elastic nature of the material. According to another embodiment of the present teachings, upon deployment, the radial expansion of at least one portion of the device is due to its pre-set thermal shape memory of the material. According to yet another embodiment of the present teachings, during deployment, at least one portion of the device is manually expanded radially via a balloon.

According to various embodiments of the present teachings, one or more radio-opaque markers are used. Without attempting to limit to any particular function, these radio-opaque markers can be visualized by using radiographic imaging equipment such as X-ray, magnetic resonance, ultrasound, or other imaging techniques known to one of ordinarily skilled in the art. One or more markers as disclosed herein can be applied to any part of a device or a delivery system of the present teachings. A radio-opaque marker can be weld, sewed, adhered, swaged riveted, otherwise placed, and secured in or on the device. The radio-opaque marker may be made of tantalum, tungsten, platinum, irridium, gold, or alloys of these materials or other materials that are known to those skilled in the art. The radio-opaque marker can also be made of numerous paramagnetic materials, including one or more elements with atomic numbers 21-29, 42, 44, and 58-70, such as chromium (III), manganese (II), iron (III), iron (II), cobalt (II), copper (II), nickel (II), praesodymium (III), neodymium (III), samarium (III), ytterbium (III), gadolinium (III), terbium (III), dysprosium (III), holmium (III) and erbium (III), or other MR visible materials that are known to those skilled in the arts.

The devices described above may be delivered by delivery systems described, e.g., in US 2011/0071623.

In most cases, the treatment starts with a septal puncture which creates an aperture in the atrial septum, and device as described above is then deployed across the aperture. Since the resulting aperture is essentially a fresh wound, the body's natural healing process will start. In some cases, the tissue or cell growth can extend through the openings of the device and into the tubular opening of the shunt portion of the device. In some situation, the opening created by the shunt portion of the device may be blocked or otherwise re-occluded by the tissue growth. Thus, such healing process would then undo all intended treatment over time.

Thus, in some embodiments, the entirety or at least a portion of the device is covered with a biocompatible barrier, for example, to prevent excessive tissue ingrowth. According to one embodiment, only one side of the luminal surface is covered. Advantages of covering one side of the luminal surface include the possibility of enhanced healing. It is known that living cells infiltrate a sufficiently porous covering material, such as ePTFE, and that microcapillaries may form within and across the barrier wall so that a living intima is formed along the luminal surface.

In one embodiment, the luminal surface of the shunt portion of the device is covered with a biocompatible barrier not only to prevent tissue ingrowth but also provide a thrombi-resistant to the shunt lumen. The configuration may depend on the application of the device. In some applications, for example, where a large aperture with a greater pressure differential between the two atria is present or created, placing the covering on the luminal surface (facing the blood flow) may result in an advantageous laminar flow of the blood—blood flow without significant turbulence. Another advantage of using only luminal covering can be improved anchoring of the device within the aperture afforded by interactions between the bare structure of the shunt portion of the device and the tissue wall surrounding the aperture.

In another embodiment, the abluminal surface (facing the tissue) of the shunt portion of the device is covered with a biocompatible barrier in order to prevent tissue ingrowth. In another embodiment, placing barrier material only on the abluminal surface of the shunt portion has some benefit to patients. For example, contacting blood with a metal structure may result in local, limited thrombosis. Thus, by covering the abluminal surface of the shunt portion of the device could limit thrombosis, resulting in enhanced healing without occlusion of the shunt lumen.

In yet another embodiment, the covering is placed on both the luminal and abluminal surfaces of the shunt portion. One skilled in the art should understand that the covering must be attached to the device to prevent it from detaching and perhaps forming emboli in the heart. In some embodiments, the material used as a barrier could be attach to a device through direct bonding between the device and material. For material that does not adhere well to a device, it can be made to bond to itself. For example, one effective method of affixing the ePTFE cover is to place ePTFE covers in contact with both the abluminal and luminal surfaces of the shunt portion of the device so that one ePTFE covering can bond to the other where the ePTFE coverings come to contact through the openings in the shunt portion.

In the embodiment where both luminal and abluminal surfaces of the shunt portions is encapsulated with same or similar material, porosity of material can be selected to achieve the best treatment result. For example, material with small pores, or even no pores could be used to encapsulate the abluminal side so that tissue encroachment can be prevented, and material with a larger pore size than that of the material covering the abluminal surface of the shunt portion could be used to cover the luminal surface in order to facilitate cell coverage and endothelialization of the luminal side to produce a thromboresistant surface in direct blood contact.

One skilled in the art would understand that the optimal configuration of the covering will have to be determined by clinicians based on each patient's conditions. The specific embodiments discussed herein should not be viewed as limiting.

In some embodiments, the encapsulating layers are made of a flexible, biocompatible, non-absorbable polymeric material (i.e., a material that does not dissolve after implanted in the body). Examples of such materials include, without limitation, expanded polytetrafluoroethylene (ePTFE), unexpanded porous PTFE, woven or knitted polyester or expanded PTFE yarns, ultrahigh molecular weight polyethylene (UHMWPE), other polyolefins, composite materials such as ePTFE with PTFE fibers, or UHMWPE film with embedded UHMWPE fibers, polyimides, silicones, polyurethane, hydrogels, fluorinated ethylene polypropylene (FEP), polypropylfluorinated amines (PFA), other related fluorinated polymers. According to another embodiments, the encapsulating layer could also be made of other material such as polyurethanes, metallic materials, polyvinyl alcohol (PVA), extracellular matrix (ECM) isolated from a mammalian tissue, or other bioengineered materials, or other natural materials (e.g., collagen), or combinations of these materials. Suitable material also include nonwoven fabrics, electrospun, dry spun materials or various combinations thereof.

Furthermore, the surface of the encapsulation material can be modified with biological, pharmaceutical and/or other active ingredients, such as anti-coagulants, anti-thrombogenic agents, cells, growth factors and/or drugs to diminish calcifications, protein deposition, and thrombus, which control and direct tissue growth by stimulating an irritation response to induce cell proliferation in one area and discourage cell proliferation in the other.

The methods and devices disclosed herein are useful for treating various symptoms of heart failures, in particular diastolic heart failures, by reducing the pressure in the left atrium and pulmonary veins. One skilled in the art would further recognize that devices according to the present teachings could be used to regulate pressure in other parts of the heart and/or vascular portions of the body. For example, the devices disclosed herein can be deployed on the septum between the left and right atria, the left and right ventricles, the left atrium and the coronary sinus, and the like.

Various embodiments have been illustrated and described herein by way of examples, and one of ordinary skill in the art would recognize that variations can be made without departing from the spirit and scope of the present teachings. The present teachings are capable of other embodiments or of being practiced or carried out in various other ways. Also, it is to be understood that the phraseology and terminology employed herein are for the purpose of description and should not be regarded as limiting.

Unless otherwise defined, all technical and scientific terms used herein have the same meaning as commonly understood by one of ordinary skill in the art to which this present teachings belong. Methods and materials similar or equivalent to those described herein can be used in the practice or testing of the present teachings. In case of conflict, the patent specification, including definitions, will control. In addition, the materials, methods, and examples are illustrative only and not intended to be limiting.

What is claimed is:

1. A device for implanting into an atrial septum of a patient, the device comprising:
    a core region comprising a plurality of core segments surrounding a central opening, the core region being adapted and configured to be disposed in an opening in the atrial septum;
    a distal retention region comprising a plurality of distal retention segments extending from the core segments, the distal retention segments being adapted to engage tissue on a left atrial side of the septal wall;
    a proximal retention region comprising a plurality of proximal retention segments extending from the core segments, the proximal retention segments being adapted to engage tissue on a right atrial side of the septal wall; and
    a retrieval region comprising a plurality of retrieval members each extending from an outward end of the proximal retention segments, each retrieval member comprising a connector at a proximal end, the connector being adapted to connect to a delivery system;
    the device further comprising a first configuration and a second configuration, wherein in its first configuration, the distal retention region engaging the atrial septum in the left atrium, and the proximal retention region engaging the atrial septum in the right atrium, while the plurality of retrieval members extend in an elongated profile, and the connectors at the proximal end of each retrieval member are proximate to each other, and wherein in its second configuration, the distal retention region engaging the atrial septum in the left atrium, and the proximal retention region engaging the atrial septum in the right atrium, while the connectors at the proximal end of the retrieval members are disposed radially outward from the central opening of the core region.

2. The device of claim 1 wherein the connectors are disposed more radially inward in the first configuration than in the second configuration.

3. The device of claim 1 wherein the retrieval region comprises two retrieval members.

4. The device of claim 1 wherein the retrieval region comprises four retrieval members.

5. The device of claim 1 wherein the connectors comprise eyelets.

6. The device of claim 1 wherein the connectors extend radially inward from an end of the retrieval members in the second configuration.

7. The device of claim 1 wherein the connectors extend distally from an end of the retrieval members in the second configuration.

8. The device of claim 1 wherein the device further comprises a retrieval configuration in which the connectors are disposed radially inward from second configuration positions and the proximal and distal retention segments are each in substantially same positions as in the second configuration.

9. The device of claim 8 wherein the retrieval members extend further proximally from the proximal retention region in the first configuration than in the retrieval configuration.

10. A method of implanting a pressure relief device in an atrial septum of a patient's heart, the device comprising a retrieval portion, a proximal retention region, a distal retention region, and a core region with an opening, wherein the retrieval region has a plurality of retrieval members each extending from an outward end of the proximal retention segments and is proximal to the proximal retention region, the device comprising a first configuration and a second configuration, wherein in its first configuration, the distal retention region engaging the atrial septum in the left atrium, and the proximal retention region engaging the atrial septum in the right atrium, while the plurality of retrieval members extend in an elongated profile, and the connectors at the proximal end of each retrieval member are proximate to each other, and wherein in its second configuration, the distal retention region engaging the atrial septum in the left atrium, and the proximal retention region engaging the atrial septum in the right atrium, while the plurality of retrieval members of the retrieval region is disposed radially outward from the opening of the core region, the method comprising:
    expanding the device into its first configuration, wherein the distal retention region, comprising a plurality of flexible retention segments, engages the septal wall in a left atrium of the patient's heart, the proximal retention region, comprising a plurality of flexible retention segments, engages the septal wall in a right atrium of the patient's heart, and the core region is positioned within an opening in the septal wall between the left atrium and the right atrium of the patient's heart;
    releasing the retrieval members from the delivery system; and thereby letting the device transition into its second configuration.

11. The method of claim 10 wherein the moving step comprises moving the retrieval members from a position proximal to the opening and radially inward from an outer boundary of the opening to a position radially outward from the outer boundary of the opening.

12. The method of claim 10 wherein the device further comprises a retrieval configuration in which the retrieval members are in a position in front of the opening and the proximal and distal retention regions are each in substantially same positions as in the second configuration, the method further comprising expanding the device to the retrieval configuration prior to the releasing step, the steps of expanding the distal retention region, core region and proximal retention region to the second configurations being performed after the releasing step.

* * * * *